US012741012B2

(12) United States Patent
Yang et al.

(10) Patent No.: US 12,741,012 B2
(45) **Date of Patent: *Sep. 22, 2026**

(54) APPLICATION OF PEG-INTERFERON AND PROTOONCOGENE PRODUCT TARGETING INHIBITOR IN SYNERGISTIC INHIBITION OF TUMORS

(71) Applicant: SHANGHAI INSTITUTE OF BIOLOGICAL PRODUCTS CO., LTD., Shanghai (CN)

(72) Inventors: Yufeng Yang, Shanghai (CN); Cheng He, Shanghai (CN); Jueren Lou, Shanghai (CN)

(73) Assignee: SHANGHAI INSTITUTE OF BIOLOGICAL PRODUCTS CO., LTD., Shanghai (CN)

( * ) Notice: Subject to any disclaimer, the term of this patent is extended or adjusted under 35 U.S.C. 154(b) by 1212 days.

This patent is subject to a terminal disclaimer.

(21) Appl. No.: 17/754,351

(22) PCT Filed: Dec. 31, 2019

(86) PCT No.: PCT/CN2019/130749

§ 371 (c)(1),
(2) Date: May 4, 2022

(87) PCT Pub. No.: WO2021/062961

PCT Pub. Date: Apr. 8, 2021

(65) Prior Publication Data

US 2022/0370565 A1 Nov. 24, 2022

(30) Foreign Application Priority Data

Sep. 30, 2019 (CN) ........................ 201910943896.X

(51) Int. Cl.
*A61K 38/21* (2006.01)
*A61P 35/00* (2006.01)

(52) U.S. Cl.
CPC ............ *A61K 38/212* (2013.01); *A61P 35/00* (2018.01)

(58) Field of Classification Search
None
See application file for complete search history.

(56) References Cited

U.S. PATENT DOCUMENTS

| | | | | |
|---|---|---|---|---|
| 5,595,756 | A * | 1/1997 | Bally | A61K 9/1272 264/4.1 |
| 9,334,331 | B2 * | 5/2016 | Igawa | A61P 43/00 |
| 10,421,807 | B2 * | 9/2019 | Gonzales | A61P 43/00 |
| 2020/0143295 | A1 * | 5/2020 | Sakurada | B60W 60/0025 |

FOREIGN PATENT DOCUMENTS

| | | | | |
|---|---|---|---|---|
| CN | 1634993 | A | 7/2005 | |
| CN | 105007896 | A | 10/2015 | |
| EP | 2789628 | A2 | 10/2014 | |
| JP | 2008509889 | A | 4/2008 | |
| JP | 2013538856 | A | 10/2013 | |
| JP | 2014533956 | A | 12/2014 | |
| JP | 2022549741 | A | 11/2022 | |
| WO | WO-2012044684 | A2 * | 4/2012 | A61P 35/00 |

OTHER PUBLICATIONS

Gayvert (PLoS Comput Biol. Jan. 13, 2017;13(1):e1005308) (Year: 2017).*
Yin et al (Front Pharmacol. 2018; 9: 535) (Year: 2018).*
Tallarida et al. Pharmacol. Ther. 2010; 127, 165-174) (Year: 2010).*
Skolnick et al (Trends Biotechnol. Jan. 2000;18(1):34-9) (Year: 2000).*
Burgess et al. (J. Cell Biol. 111:2129-2138, 1990) (Year: 1990).*
Miosge (Proc Natl Acad Sci U S A. Sep. 15, 2015;112(37):E5189-98) (Year: 2015).*
Bork (Genome Research, 2000, 10:398-400) (Year: 2000).*
Kulmanov et al (Bioinformatics, 34(4), 2018, 660-668) (Year: 2018).*
Vattekatte, (Peer J, DOI 10.7717/peerj.8408) (Year: 2019).*
Edwards et al. (2003, JMB 334:103-118) (Year: 2003).*
Lloyd et al. (2009, Protein Engineering, Eng. Design & Selection 22(3): 159-168) (Year: 2009).*
Goel et al. (2004, J. Immunol. 173: 7358-7367) (Year: 2004).*
Khan et al. (2014, J. Immunol. 192: 5398-5405) (Year: 2014).*
Poosarla et al. (2017, Biotechn. Bioeng. 114(6): 1331 -1342) (Year: 2017).*
Rabia, et al. (2018, Biochemical Engineering Journal 137:365-374) (Year: 2018).*
Vajdos et al. (J Mol Biol. Jul. 5, 2002;320(2):415-28) (Year: 2002).*
Brown et al. (J Immunol. May 1996; 156(9):3285-91) (Year: 1996).*
Guido et al (Curr Med Chem. 2008; 15(1):37-46) (Year: 2008).*
Clark et al (J. Med. Chem., 2014, 57 (12), pp. 5023-5038) (Year: 2014).*
Aagaard et al (Advanced Drug Delivery Reviews 59 (2007) 75-86) (Year: 2007).*

(Continued)

*Primary Examiner* — Brian Gangle
*Assistant Examiner* — Andrea K McCollum
(74) *Attorney, Agent, or Firm* — NKL Law; Bin Lu; Allen Xue

(57) ABSTRACT

An application of polyethylene glycol (PEG)-interferon and a protooncogene product targeting inhibitor in synergistic inhibition of tumors. Specifically, provided is use of an active ingredient combination. The active ingredient combination comprises PEG-interferon and a protooncogene product targeting inhibitor, and the combination is used for preparing a pharmaceutical composition for synergistic treatment of tumors. The active ingredient combination can synergistically inhibit the growth of tumors (especially lung, stomach, breast and liver cancers) effectively, and can significantly reduce toxic and side effects, and therefore can be widely used in targeted therapy of the tumors.

12 Claims, 10 Drawing Sheets

(56) References Cited

OTHER PUBLICATIONS

Warzocha et al (Leukemia and Lymphoma (1997) vol. 24. pp. 267-281) (Year: 1997).*
McKeague et al (J Nucleic Acids. 2012;2012:748913. Epub Oct. 24, 2012) (Year: 2012).*
Sporn et al, "Chemoprevention of Cancer," Carcinogenesis, vol. 21 (2000), 525-530 (Year: 2000).*
Auerbach et al (Cancer and Metastasis Reviews, 2000, 19: 167-172) (Year: 2000).*
Gura T (Science, 1997, 278(5340): 1041-1042, encloses 1-5) (Year: 1997).*
Jain RK (Scientific American, Jul. 1994,58-65) (Year: 1994).*
HogenEsch et al (J Control Release. Dec. 10, 2012; 164(2): 183-186.) (Year: 2012).*
Shek et al (Journal of Clinical Oncology; vol. 27, No. 15_suppl; Meeting Abstract: 2009 ASCO Annual Meeting). (Year: 2009).*
Kusano et al (International Journal of Oncology 42: 1897-1903, 2013). (Year: 2013).*
Grignol et al (J Immunother. 2011 ; 34(6): 509-515) in view of Herndon et al.(The Oncologist 2012;17:1323-1328). (Year: 2012).*
Ciardiello, F. et al.; "Cooperative inhibition of renal cancer growth by anti-epidermal growth factor receptor antibody and protein kinase A antisense oligonucleotide"; Journal of National Cancer Instrute; vol. 90, No. 14; Jul. 15, 1998. pp. 1087-1094.
Wang, Jiajing et al., "Influence of trastuzumab with Interferon a-2b on renal carcinoma cell", Journal of Medical Postgraduates, vol. 20, No. 8, Aug. 31, 2007 (Aug. 31, 2007), ISSN: 1008-8199, abstract, p. 789, right-hand column last paragraph to p. 791, right-hand column, last paragraph.
Yang. Yufeng et al., "Preparation and Properties of PEGylated Recombinant Human Interferon alb", Chinese Journal of Biologicals, vol. 23, No. 6, Jun. 30, 2010 (Jun. 30, 2010), ISSN: 1004-5503, abstract, p. 615, left-hand column, paragraph 1 to p. 618, left-hand column, paragraph 1.
Tamura, Kenji; "EGFR and VEGF-targeted drugs: clinical evidence for their effects from evaluation of biomarkers", Folia pharmacologica Japonica, vol. 133, Issue 2; Year: 2009, pp. 69-72.
Davar, Diwakar et al.; "Phase Ib/11 Study of Pembrolizumab and PegylatedInterferon Alfa-2b in Advanced Melanoma"; Journal of Clinical Oncology, vol. 36, No. 35; Published at Oct. 25, 2018; pp. 3450-3458 and 6 pages (Total 15 pages).
Shi. Jiuhua, "Non-official translation: Treatment of Metastatic Renal Cell Carcinoma Combining Bevacizumab and Interferon alpha", International Journal of Biologicals, Dec. 31, 2009, vol. 32, No. 6, pp. 305.

* cited by examiner

| PEG-interferon (μg/ml) | 9.38 | 18.75 | 37.50 | 75 | 150 | 300 | 600 |
|---|---|---|---|---|---|---|---|
| Herceptin (μg/ml) | 0.05 | 0.09 | 0.19 | 0.38 | 0.75 | 1.50 | 3 |
| PEG-interferon (μg/ml) + Herceptin (μg/ml) | 9.38 + 0.05 | 18.75 + 0.09 | 37.50 + 0.19 | 75 + 0.38 | 150 + 0.75 | 300 + 1.50 | 600 + 3.00 |

APPLICATION OF PEG-INTERFERON AND PROTOONCOGENE PRODUCT TARGETING INHIBITOR IN SYNERGISTIC INHIBITION OF TUMORS

TECHNICAL FIELD

The invention relates to the technical field of antitumor drugs, and in particular to the application and related drugs of PEG-interferons and protooncogene product targeting inhibitors in synergistic inhibition of tumors.

BACKGROUND

Tumor is a kind of systemic disease with multi-factor participation and multi-step development. Tumors have biological characteristics of high complexity, variability and diversity. Abnormalities of cancer-related genes can cause instability of tumor genome, which in turn leads to abnormal biological behaviors of tumor cells, such as evasion of apoptosis, the potential for unlimited replication, angiogenesis, invasion and metastasis, and immune escape.

At present, surgery, radiotherapy and chemotherapy are the main methods for the treatment of malignant tumors. Surgery and radiotherapy are local treatment methods, while drug treatment is a method with systemic effect, which takes into account the characteristics of spread and metastasis of malignant tumors.

Traditional tumor treatment methods, including surgery, radiotherapy and chemotherapy, have shown good efficacy, but also many disadvantages. In recent years, tumor immunotherapy has significantly improved the quality of life for patients compared with traditional tumor treatment.

However, the ineffective clinical treatment and the frequent emergence of drug resistance have prompted the need to develop more effective treatment regimens. In addition, some anti-tumor drugs have serious toxic and side effects, causing patients to give up the treatment.

Therefore, there is an urgent need in the art to develop new effective treatment methods and drugs for treating tumors with low toxic and side effects.

SUMMARY OF THE INVENTION

The purpose of the present invention is to provide an effective treatment method and medicine thereof for treating tumors with low toxic and side effects. Specifically, the present invention provides the use of a PEGylated (PEG) interferon and a protooncogene product targeting inhibitor in synergistic treatment of tumors.

In the first aspect of the present invention, it provides the use of a combination of active ingredients in preparing a pharmaceutical composition or a kit for synergistic treatment of tumors, wherein the combination comprises a first active ingredient of PEG-interferon and a second active ingredient of a protooncogene product targeting inhibitor.

In another preferred embodiment, the protooncogene product targeting inhibitor is an antibody.

In another preferred embodiment, the PEG-interferon is a PEG-interferon α1b.

In another preferred embodiment, the PEG-interferon comprises a recombinant human interferon α1b modified with PEG of 10,000-100,000 molecular weight, preferably a recombinant human interferon α1b modified with PEG of 10,000-50,000 molecular weight.

In another preferred embodiment, a mass ratio of the PEG-interferon to the protooncogene product targeting inhibitor is 1:100 to 500:1, preferably 1:20 to 200:1, and more preferably 1:10 to 100:1 or 1:5 to 50:1.

In another preferred embodiment, a ratio (IU/mg) of the PEG-interferon to the protooncogene product targeting inhibitor is 1,000 IU/mg to 100 million IU/mg, preferably 10,000 IU/mg to 10 million IU/mg, and more preferably 100,000 IU/mg to 5 million IU/mg or 200,000 IU/mg to 3 million IU/mg.

In another preferred embodiment, the pharmaceutical composition or kit is used in treatment of a mammal or is administered to a mammal, preferably rodent (e.g. mice, rat) or human.

In another preferred embodiment, the tumors are selected from the group consisting of: lung cancer, gastric cancer, breast cancer, liver cancer, intestinal cancer, ovarian cancer, cervical cancer, and combinations thereof.

In another preferred embodiment, the tumors are selected from the group consisting of: lung cancer, gastric cancer, breast cancer, and combinations thereof.

In another preferred embodiment, the protooncogene product targeting inhibitor is selected from the group consisting of: an EGFR inhibitor, a HER2 inhibitor, and combinations thereof.

In another preferred embodiment, the protooncogene product targeting inhibitor is selected from the group consisting of: an EGFR inhibitor, a HER2 inhibitor, and combinations thereof.

In another preferred embodiment, the protooncogene product targeting inhibitor is selected from the group consisting of: Bevacizumab (AVASTIN), Trastuzumab (HERCEPTIN), Pertuzumab, and combinations thereof.

In the second aspect of the present invention, it provides a pharmaceutical composition, which comprises a PEG-interferon, a protooncogene product targeting inhibitor and a pharmaceutically acceptable carrier.

In another preferred embodiment, the pharmaceutical composition further comprises an additional therapeutic drug (e.g. an antitumor agent).

In another preferred embodiment, the protooncogene product targeting inhibitor is selected from the group consisting of: an EGFR inhibitor, a HER2 inhibitor, and combinations thereof.

In another preferred embodiment, the protooncogene product targeting inhibitor is selected from the group consisting of: Bevacizumab (AVASTIN), Trastuzumab (HERCEPTIN), Pertuzumab, and combinations thereof.

In another preferred embodiment, the pharmaceutical composition further comprises a chemotherapeutic agent, a checkpoint inhibitor, CAR-T cells, and combinations thereof.

In another preferred embodiment, the chemotherapeutic agent comprises cisplatin or paclitaxel.

In the third aspect of the present invention, it provides a combination of active ingredients, which consists of a PEG-interferon and a protooncogene product targeting inhibitor.

In another preferred embodiment, the protooncogene product targeting inhibitor is selected from the group consisting of: an EGFR inhibitor, a HER2 inhibitor, and combinations thereof.

In the fourth aspect of the present invention, it provides a kit comprising:

(a) a first preparation comprising a PEG-interferon and a pharmaceutically acceptable carrier;

(b) a second preparation comprising a protooncogene product targeting inhibitor and a pharmaceutically acceptable carrier; and (c) an instruction describing a method of combining the PEG-interferon with the protooncogene product targeting inhibitor for tumor treatment.

In another preferred embodiment, the first preparation and the second preparation are separate from one another.

In another preferred embodiment, the first preparation and the second preparation are lyophilized preparation or liquid preparation.

In another preferred embodiment, the first preparation and the second preparation are injection.

In another preferred embodiment, the first preparation is administered before, during or after the administration of the second preparation.

In another preferred embodiment, the protooncogene product targeting inhibitor is selected from the group consisting of: an EGFR inhibitor, a HER2 inhibitor, and combinations thereof.

In another preferred embodiment, the protooncogene product targeting inhibitor is selected from the group consisting of: Bevacizumab (AVASTIN), Trastuzumab (HERCEPTIN), Pertuzumab, and combinations thereof.

In the fifth aspect of the present invention, it provides a non-therapeutic method in vitro for synergistic inhibition on the growth of tumor cells, which comprises the following steps: adding the pharmaceutical composition according to the second aspect of the present invention and/or the combination of active ingredients according to the third aspect of the present invention to a culture system for tumor cells, thereby synergistically inhibiting the growth of tumor cells.

In another preferred embodiment, the method comprises: co-culturing the tumor cells with the PEG-interferon and the protooncogene product targeting inhibitor.

In another preferred embodiment, the tumor cells comprise tumor cells in logarithmic growth phase.

In another preferred embodiment, the number of tumor cells is $10^3$-$10^8$ cells/ml.

In another preferred embodiment, the culture time is 0.1-120 hours, and preferably 1-96 hours.

In another preferred embodiment, a final concentration of the PEG-interferon in the mixed medium is 100-1,000 μg/ml, preferably 200-500 μg/ml, and more preferably about 300 μg/ml.

In another preferred embodiment, a final concentration of the protooncogene product targeting inhibitor in the mixed medium is 0.5-50 μg/ml, preferably 1-25 μg/ml, more preferably 2-15 μg/ml, for example, about 3 μg/ml.

In another preferred embodiment, a mass ratio of the PEG-interferon to the protooncogene product targeting inhibitor is 1:100 to 500:1, preferably 1:20 to 200:1, and more preferably 1:10 to 100:1 or 1:5 to 50:1.

In another preferred embodiment, a ratio (IU/mg) of the PEG-interferon to the protooncogene product targeting inhibitor is 1,000 IU/mg to 100 million IU/mg, preferably 10,000 IU/mg to 10 million IU/mg, and more preferably 100,000 IU/mg to 5 million IU/mg or 200,000 IU/mg to 3 million IU/mg.

In the sixth aspect of the present invention, it provides a method for treating tumors, which comprises the following steps: administering the pharmaceutical composition according to the second aspect of the present invention and/or the combination of active ingredients according to the third aspect of the present invention to a subject (e.g., a human) in need, thereby treating tumor cells.

In the seventh aspect of the present invention, it provides a method for reducing toxic and side effects of a protooncogene product targeting inhibitor, which comprises the following steps: administering a PEGylated (PEG) interferon to a subject (e.g., a human) in need, wherein the PEGylated (PEG) interferon is administered to the subject before, during and/or after the administration of a protooncogene product targeting inhibitor.

In another preferred embodiment, the toxic and side effects are selected from the group consisting of: weight loss, gastrointestinal reactions (such as nausea, vomiting and loss of appetite), fatigue, rash and erythema.

It should be understood that within the scope of the present invention, the above-mentioned technical features of the present invention and the technical features specifically described in the following (such as the embodiments) can be combined with each other to form a new or preferred technical solution, which are not redundantly repeated one by one due to space limitation.

DETAILED DESCRIPTION

Figure 1:
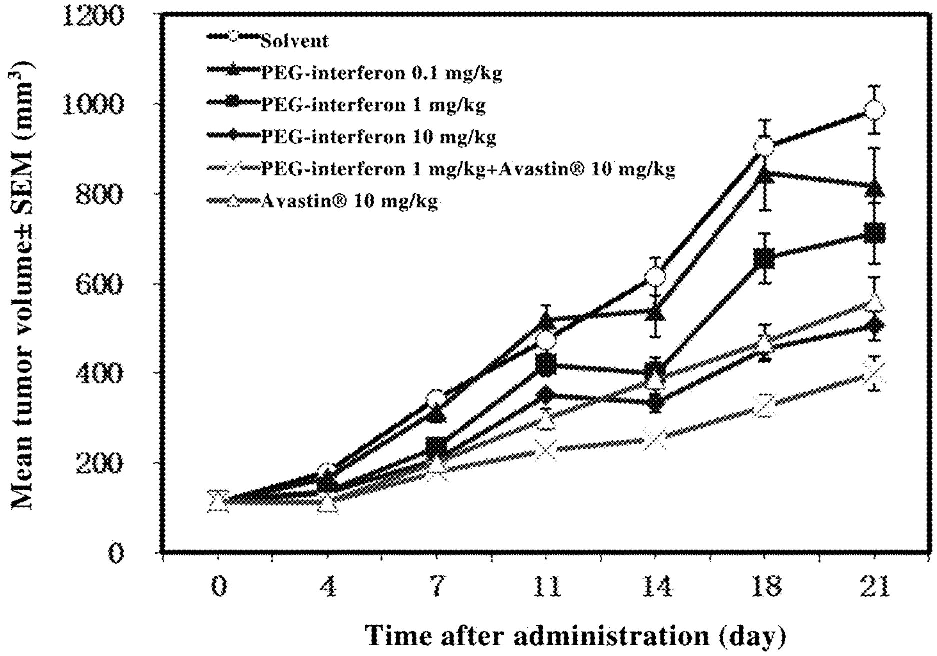
FIG. 1 shows the therapeutic effects of using PEGylated (PEG) interferon or Bevacizumab (AVASTIN) alone or in combination on subcutaneous transplanted tumors of human gastric cancer NCI-N87 in nude mice.

After extensive and intensive research and massive screening, the inventors have unexpectedly discovered for the first time that a PEGylated (PEG) interferon and a protooncogene product targeting inhibitor have a satisfactory synergistic effect in the treatment of tumors (especially breast cancer and gastric cancer). The combined use of the PEGylated (PEG) interferon and the protooncogene product targeting inhibitor can effectively inhibit tumor growth, and its effect is far better than the additive effect of both. Besides, side effects which occur when using interferons (especially those caused by long-term use of interferon drugs at high doses) can be significantly reduced by the combined use. On this basis, the inventors have completed the present invention.

Terms

As used herein, the term "a first active ingredient" refers to a PEGylated (PEG) interferon or PEG-interferon. It should be understood that the term comprises derivatives with the same function as PEGylated (PEG) interferons.

As used herein, the term "a second active ingredient" refers to a protooncogene product targeting inhibitor, especially a small molecule targeting inhibitor and an antibody-based targeting inhibitor. Preferably, the protooncogene product is a protein, such as EGFR protein, Her2 protein and the like.

As used herein, the terms "a combination of active ingredients of the invention", "a combination of substances of the invention" and "a combination of pharmaceutical ingredients of the invention" are used interchangeably, referring to a combination of the first active ingredient and the second active ingredient described above.

As used herein, the term "a pharmaceutical composition of the invention" refers to a composition which comprises a first active ingredient (or a first preparation comprising the first active ingredient) and a second active ingredient (or a second preparation comprising the second active ingredient), wherein the first preparation and the second preparation may be the same or different preparations. Furthermore, the first preparation and the second preparation may be one single preparation or independent two preparations.

Ordinary Interferon and PEGylated (PEG) Interferons

As an important member of tumor immunotherapy, ordinary interferons (IFN) therapy has been used in tumor treatment for many years. A large number of studies have shown that ordinary interferons have well performance in the inhibition of the growth of a variety of tumors.

Ordinary interferon α was approved as the first biological agent for the treatment of malignant tumors in 1986. Currently, it has a wide range of indications, including hairy cell leukemia, chronic leukemia, non-Hodgkin's lymphoma, myeloma, bladder cancer, ovarian cancer, advanced metastatic renal cancer and pancreatic malignant endocrine tumors, melanoma, laryngeal papilloma, basal cell carcinoma and Kaposi sarcoma, etc.

Ordinary interferon α1b (rhIFNα1b) is the first genetically engineered protein drug in China that was cloned and developed from the leukocytes of the umbilical cord blood of healthy Chinese people in the 1980s.

rhIFNα1b consists of 166 amino acids with a relative molecular weight of 19.382 kDa, and it has broad-spectrum antiviral, antitumor and immunomodulatory activities. Depending on the results of clinical researches conducted in the 1990s and the effects of clinical research and application in the past few decades, it has been proved to have a certain therapeutic effect on certain tumors. However, treatment with interferons alone requires the use of high doses and causes serious side effects and poor patient compliance.

```
Amino acid sequences and homology analysis of interferon α isoforms
HuIFNα-1b (166aa) ACCESSION: AAL35223
                                                        (SEQ ID No.: 1)
  1     CDLPETHSLD NRRTLMLLAQ MSRISPSSCL MDRHDFGFPQ EEFDGNQFQK

 51     APAISVLHEL IQQIFNLFTT KDSSAAWDED LLDKFCTELY QQLNDLEACV

101     MQEERVGETP LMNADSILAV KKYFRRITLY LTEKKYSPCA WEVVRAEIMR

151     SLSLSTNLQE RLRRKE                                    166

HuIFNα-2a (165aa) ACCESSION: 1ITF_A
                                                        (SEQ ID No.: 2)
  1     CDLPQTHSLG SRRTLMLLAQ MRKISLFSCL KDRHDFGFPQ EEFGNQFQKA

 51     ETIPVLHEMI QQIFNLFSTK DSSAAWDETL LDKFYTELYQ QLNDLEACVI

101     QGVGVTETPL MKEDSILAVR KYFQRITLYL KEKKYSPCAW EVVRAEIMRS

151     FSLSTNLQES LRSKE                                     165

HuIFNα-2b (165aa) ACCESSION: 1RH2_A
                                                        (SEQ ID No.: 3)
  1     CDLPQTHSLG SRRTLMLLAQ MRRISLFSCL KDRHDFGFPQ EEFGNQFQKA

 51     ETIPVLHEMI QQIFNLFSTK DSSAAWDETL LDKFYTELYQ QLNDLEACVI

101     QGVGVTETPL MKEDSILAVR KYFQRITLYL KEKKYSPCAW EVVRAEIMRS

151     FSLSTNLQES LRSKE                                     165
```

-continued

```
Homology analysis: NCBI BLAST
HuIFN-1b and HuIFN-2a: 81%
Query     1  CDLPETHSLDNRRTLMLLAQMSRISPSSCLMDRHDFGFPQEEFDGNQFQKAPAISVLHEL   60

             CDLP+THSL +RRTLMLLAQM +IS SCL DRHDFGFPQEEF GNQFQKA             1
             VLHE+

Sbjct     1  CDLPQTHSLGSRRTLMLLAQMRKISLFSCLKDRHDFGFPQEEF-GNQFQKAETIPVLHEM   59

Query    61  IQQIFNLFTTKDSSAAWDEDLLDKFCTELYQQPNDLEACVMQEERVGETPLMNADSILAV  120
             IQQIFNLF+TKDSSAAWDE LLDKF TELYQQ NDLEACV+Q V ETPLM
             DSILAV

Sbjct    60  IQQIFNLFSTKDSSAAWDETLLDKFYTELYQQLNDLEACVIQGVGVTETPLMKEDSILAV  119

Query   121  KKYFRRITLYLTEKKYSPCAWEVVRAEIVRSLSLSTNLQERLRRKE               166
             +KYF+RITLYL EKKYSPCAWEVVRAEI+RS SLSTNLQE LR KE

Sbjct   120  RKYFQRITLYLKEKKYSPCAWEVVRAEIMRSFSLSTNLQESLRSKE               165

HuIFN-1b and HuIFN-2b: 83%
Query     1  CDLPETHSLDNRRTLMLLAQMSRISPSSCLMDRHDFGFPQEEFDGNQFQKAPAISVLHEL   60

             CDLP+THSL +RRTLMLLAQM RIS SCL DRHDFGFPQEEF GNQFQKA             1
             VLHE+

Sbjct     1  CDLPQTHSLGSRRTLMLLAQMRRISLFSCLKDRHDFGFPQEEF-GNQFQKAETIPVLHEM   59

Query    61  IQQIFNLFTTKDSSAAWDEDLLDKFCTELYQQPNDLEACVMQEERVGETPLMNADSILAV  120
             IQQIFNLF+TKDSSAAWDE LLDKF TELYQQ NDLEACV+Q V ETPLMN
             DSILAV

Sbjct    60  IQQIFNLFSTKDSSAAWDETLLDKFYTELYQQLNDLEACVIQGVGVTETPLMNEDSILAV  119

Query   121  KKYFRRITLYLTEKKYSPCAWEVVRAEIVRSLSLSTNLQERLRRKE               166
             +KYF+RITLYL EKKYSPCAWEVVRAEI+RS SLSTNLQE LR KE

Sbjct   120  RKYFQRITLYLKEKKYSPCAWEVVRAEIMRSFSLSTNLQESLRSKE               165
```

Polyethylene Glycol (PEG) is a general term for ethylene glycol polymers with a linear or branched structure and an average molecular weight of more than 200 Da. It has the characteristics of high molecular weight, safety and non-toxicity, amphiphilicity, immune inertness and structural stability, etc. Chemical modification of a protein with polyethylene glycol can prolong the half-life of the protein in vivo, improve its stability, reduce immunogenicity and antigenicity thereof, and etc., without changing the amino acid composition of protein. It is a simple and effective method to improve the pharmacodynamic properties of protein drugs.

A preferred PEGylated (PEG) interferon α1b is a recombinant human interferon α1b modified with PEG of about 10,000-100,000 Daltons (e.g. about 20,000). A particularly preferred PEGylated (PEG) interferon α1b is a recombinant human interferon α1b modified with PEG having a molecular weight of about 20,000 Daltons, and is a new type of long-acting interferon α1b drugs (see Chinese Patent ZL200410067652.3). It was observed in vitro that the PEGylated (PEG) interferon α1b could inhibit the proliferation of tumor cells. In addition, it was observed in vivo that the PEGylated (PEG) interferon α1b had obvious therapeutic effects on subcutaneous transplanted tumors in mice.

In vitro experiments showed that the PEGylated (PEG) interferon α1b could inhibit the proliferation of tumor cells and exert its antitumor effects by activating JAK/STAT signal pathway. It could inhibit the growth of vascular endothelial cells and promote their apoptosis by inhibiting the expression of tumor angiogenesis factors.

Preferably, when the PEGylated (PEG) interferon α1b is used in combination with the monoclonal antibody agent Bevacizumab (AVASTIN), the tumor inhibition rate of human gastric cancer NCI-N87 and other tumor cells can be significantly increased, indicating that PEGylated (PEG) interferon α1b has a synergistic effect on the treatment of subcutaneous transplanted tumors of human gastric cancer in nude mice with Bevacizumab (AVASTIN).

Preferably, when the PEGylated (PEG) interferon α1b is used in combination with the monoclonal antibody agent Trastuzumab (HERCEPTIN), the tumor inhibition rate of human breast cancer BT-474 and other tumor cells can be significantly increased, indicating that PEGylated (PEG) interferon α1b has a synergistic effect on the treatment of subcutaneous transplanted tumors of human breast cancer in nude mice with Trastuzumab (HERCEPTIN).

In addition, when the first active ingredient of PEGylated (PEG) interferon and the second active ingredient of protooncogene product targeting inhibitor (such as Bevacizumab (AVASTIN) or Trastuzumab (HERCEPTIN), etc.) are used in combination, it can not only effectively inhibit tumors, but also significantly reduce toxic and side effects, especially one or more adverse reactions selected from the group consisting of: influenza-like syndrome, gastrointestinal reactions (e.g., nausea, vomiting, loss of appetite), fatigue, rash (including non-specific rash with pruritus), erythema, etc., and weight loss.

The study of the present invention also shows that a PEGylated (PEG) interferon can inhibit the growth and/or migration of tumor cells when administered to the tumor cells.

Protooncogene Product Targeting Inhibitor

As used herein, the terms "protooncogene product targeting inhibitor" and "protooncoprotein targeting inhibitor" are used interchangeably and refer to inhibitors that specifically target the encoding products (especially proteins) of the protooncogene. As used herein, the term "protooncoprotein" refers to a protein encoded by a protooncogene, especially a membrane protein. In some embodiments of the present invention, a protooncoprotein inhibitor may exert its functions by reducing the amount of a protooncoprotein, inhibiting or blocking the activation of a protooncoprotein, or inhibiting other molecules in a signaling pathway.

Non-limiting embodiments of a protooncogene product targeting inhibitor include, (but are not limited to,) EGFR-targeting inhibitors, Her2-targeting inhibitors, and combinations thereof.

As used herein, the term "protooncoprotein activity" refers to the ability of a protooncoprotein to promote the formation, growth, proliferation, migration and/or invasion of cancer cells.

As used herein, the term "protooncoprotein expression" refers to the formation of a protooncoprotein gene product as measured by any method known in the art, including (but not limited to): nucleic acid hybridization methods, Northern blotting, protooncoprotein site hybridization, polymerase chain reaction amplification, reporter gene expression, etc. The formation of protooncoprotein gene products can also be measured by any antibody-based technique, including immunohistochemistry, immunofluorescence, Western blotting, and ELISA methods.

In the present invention, targeting inhibitors include (but are not limited to): antibodies, small molecule drugs, nucleic acid drugs, CAR-T cells, and the like.

EGFR and Inhibitors Thereof

Epidermal growth factor receptor (EGFR) is a transmembrane protein (NM_201282) and a member of ErbB receptor family. Its ligands (EGF, TGF-α, etc.) bind to the extracellular segment of EGFR to dimerize, which leads to the activation of intracellular tyrosine kinases and a series of cascade reaction in signal transduction, i.e. promoting cell proliferation, angiogenesis, metastasis and inhibition of apoptosis, and thereby leading to tumorigenesis. In a large number of studies, it is found that EGFR gene is overexpressed or abnormally activated in various tumor tissues, thereby enhancing the ability of tumor cells to proliferate, invade and metastasize. EGFR has become a clinically validated therapeutic target for many types of tumors.

In the development of target treatment for cancer, a successful strategy is using monoclonal antibodies (mAbs) to localize epitopes on the surface of tumor cells, so as to target then kill cancer cells. Therefore, antibodies or other targeting inhibitors may be used for targeting EGFR on the surface of tumor cells to kill or inhibit them.

A representative EGFR inhibitor is an anti-EGFR antibody such as Bevacizumab (AVASTIN), biosimilars or ADC thereof. The Bevacizumab is an anti-EGFR monoclonal antibody.

Her2 and Inhibitors Thereof

The HER family of receptor tyrosine kinases are important mediators of cell growth, differentiation and survival. The receptor family comprise four distinct members: HER1 (EGFR or ErbB1), Her2 (ErbB2 or p185neu), HER3 (ErbB3) and HER4 (ErbB4 or tyro2).

Although Her2 can not directly interact with HER-activating ligands, it is well established that its kinases enable heterodimers containing Her2 to transmit signals and may increase the affinity of ligands for binding to EGFR or HER3. The formation of Her2 dimer triggers a series of processes in cells that ultimately lead to increased cell motility, cell viability and proliferation, and anti-apoptotic activity.

Similarly, antibodies or other targeting inhibitors may be used for targeting the Her2 antigen on the surface of tumor cells to kill or inhibit them.

A representative Her2 inhibitor is Trastuzumab (HERCEPTIN) or biosimilars or ADC thereof. Trastuzumab is a humanized anti-Her2 monoclonal antibody that binds to Region IV of the cell surface region of Her2.

In addition to Trastuzumab, Pertuzumab (PERJETA) is also a humanized Her2-specific monoclonal antibody. Unlike Trastuzumab, Pertuzumab binds to Region II of the cell surface region of Her2, thereby preventing Her2 from binding to other members of the HER family. Pertuzumab has demonstrated clinical efficacy against ovarian cancer, non-small cell lung cancer, prostate cancer, breast cancer, and gastric cancer.

RNAi, siRNA, shRNA

In the present invention, nucleic acid drugs targeting protooncogenes can also be used to target and inhibit the protooncogenes (e.g., EGFR or Her2).

Representative nucleic acid drugs include (but are not limited to): RNAi, siRNA, shRNA, and precursors or expression vectors thereof.

As used herein, the term "RNAi" (RNA interference) refers to a phenomenon of efficient and specific degradation of homologous mRNA, which is highly conserved in evolution and induced by double-stranded RNA (dsRNA). Since the use of RNAi technology can specifically knock out or turn off the expression of specific genes, this technology has been widely used in exploring gene functions and in the field of gene therapy for infectious diseases and malignant tumors.

As used herein, the term "siRNA" (Small interfering RNA, siRNA) refers to a small RNA molecule (about 21-25 nucleotides) that can be processed by Dicer (an enzyme in the RNAase III family that is specific to double-stranded RNA) from its precursors (such as dsRNA, shRNA, etc.), and can also be synthesized by chemical methods or processed by other proteins. siRNA is a main member of siRISC, which stimulates its complementary target mRNA to be rapidly cleaved and degraded, resulting in the silencing of the target gene, thus becoming a key functional molecule in RNAi.

As used herein, the term "expression cassette" refers to an expression cassette comprising a coding sequence of an RNAi precursor of the present invention and a promoter and termination signal operably linked to the coding sequence, which generates the RNAi precursor of the present invention after transcription. The term "RNAi precursor" as used herein refers to an RNA molecule that can be processed in mammalian cells to produce siRNA. Specifically, the RNAi precursor is selectively processed by Dicer, Ago2 or other similar proteins to produce mature siRNA for RNAi.

As used herein, the term "shRNA" is an abbreviation for short hairpin RNA. shRNA consists of two short reverse complementary sequences, and the middle of the shRNA is separated by an apical loop sequence, forming a hairpin structure. The transcription of shRNA is regulated by an endogenous RNA polymerase III promoter, and the end of the shRNA sequence is connected with 5-6 T as a transcription terminator of the RNA polymerase III. One way to generate a "small interfering RNA" (siRNA) in vivo is to clone the siRNA sequence into a plasmid vector as part of a "short hairpin". When delivered into animals, the hairpin sequence is expressed to form a "double-stranded RNA" (shRNA) with an apical loop structure, which is recognized and processed by proteins such as Dicer and Ago2 in cells to produce a functional siRNA.

As used herein, the term "miRNA" (microRNA) is a class of non-coding single-stranded RNA molecules of about 20-24 nucleotides in length encoded by endogenous genes, which are involved in the expression regulation of a large number of genes in animals and plants. So far, more than 4,000 miRNA molecules have been found in animals, plants and viruses. Most miRNA genes exist in the genome in the form of single copy, multiple copies or gene clusters. Each miRNA can regulate multiple target genes, and several miRNAs can also participate in regulating the same gene together, forming a complex regulatory network. It is speculated that miRNAs regulate the expression of more than half of human genes. There are many forms of miRNA, and the most primitive one is a pri-miRNA; after the pri-miRNA is processed by Drosha, it becomes a pre-miRNA, i.e., a miRNA precursor, with a length of about 50-90 nucleotides; after the pre-miRNA is digested by Dicer enzyme, it becomes a mature miRNA with a length of about 20-24 nucleotides. The miRNA inhibits the expression of a target gene mainly by inhibiting translation and accelerating deadenylation of the mRNA, and the mechanism thereof is different from siRNA-mediated mRNA degradation.

Expression Vector

As used herein, the term "expression vector" refers to a vector capable of transferring a polynucleotide sequence of interest to a target cell. Such vectors can self-replicate or integrate into host cell chromosomes (host cells include, e.g., prokaryotic cells, yeasts, animal cells, plant cells, insect cells, animal individuals, and plant individuals, etc.), and may contain promoters at sites suitable for transcription of the polynucleotides of the present invention. Expression vectors may contain structural genes and promoters that regulate their expression. Moreover, various regulatory elements that function in the host cells may also be contained. It is well known in the art that the type of expression vectors for a living organism (e.g., an animal) and the type of regulatory elements used can vary depending on the type of host cells used.

A viral vector that can be used in the present invention is not particularly limited, and may be any viral vector that can transmit its genome based on its characteristics to introduce genetic materials into other cells for infection. The introduction of genetic materials into other cells can occur in a whole, living organism or in cell culture. Viral vectors comprise lentiviral vectors, adenoviral vectors, herpesvirus vectors, and poxvirus vectors. In the present invention, a preferred expression vector is a lentiviral vector.

Pharmaceutical Composition and Administration Method

In the present invention, it also provides a composition that can be used in synergistic treatment for tumors, which can be used to inhibit the growth and/or metastasis of the tumors.

The pharmaceutical composition of the present invention comprises: an effective amount of a PEGylated (PEG) interferon, an effective amount of a protooncogene product targeting inhibitor, and a pharmaceutically acceptable carrier.

In addition, the pharmaceutical composition of the present invention may also comprises optional chemotherapeutic agents for solid tumors. The chemotherapeutic agents include (but are not limited to) cisplatin, paclitaxel, doxorubicin and the like.

In general, the PEGylated (PEG) interferon, or the protooncogene product targeting inhibitor of the present invention can be formulated in a non-toxic, inert and pharmaceutically acceptable carrier medium, wherein the pH is usually about 5-8, preferably, the pH is about 6-8.

As used herein, "pharmaceutically acceptable carrier" refers to a carrier for administration of a therapeutic agent, comprising various excipients and diluents.

The term refers to pharmaceutical carriers which are not themselves essential active ingredients and are not unduly toxic after administration. Suitable carriers are well known to those skilled in the art. Pharmaceutically acceptable carriers in the composition may contain liquids such as water, saline, and buffers. In addition, auxiliary substances such as fillers, lubricants, glidants, wetting or emulsifying agents, pH buffering substances and the like may also be present in these carriers. The carriers may also contain cell transfection reagents.

As used herein, the term "effective amount" or "effective dose" refers to an amount that is functional or active in humans and/or animals and/or cells and is acceptable to humans and/or animals.

As used herein, a "pharmaceutically acceptable" ingredient is a substance that is suitable for use in humans and/or mammals without undue adverse side effects (such as toxicity, irritation, and allergy), i.e., a substance with a reasonable benefit/risk ratio. The term "pharmaceutically acceptable carrier" refers to a carrier for administration of a therapeutic agent, comprising various excipients and diluents. Such carriers include (but are not limited to) saline, buffers, dextrose, water, glycerol, polysorbates, ethanol, and combinations thereof. Usually, a pharmaceutical preparation should be matched to the administration method, and the pharmaceutical composition of the present invention can be prepared in the form of injection, for example, prepared by conventional methods with normal saline or an aqueous solution containing glucose and other adjuvants. The pharmaceutical composition is preferably manufactured under sterile conditions. The dosage of an active ingredient is a therapeutically effective amount. The pharmaceutical preparation of the present invention may also be made into a sustained-release preparation.

Furthermore, a combination of active ingredients of the present invention may also be used with other therapeutic agents (such as antineoplastic or immunomodulatory agents).

When using a pharmaceutical composition, a safe and effective amount of a composition of active ingredients (comprising the first active ingredient (or a formulation thereof) and/or the second active ingredient (or a formulation thereof)) is administered to the mammals.

It should be understood that the effective amount of the first active ingredient (or a formulation thereof) and/or the second active ingredient (or a formulation thereof) in the combination of active ingredients of the present invention may vary with the mode of administration and the severity of the tumor, etc. Selection of the preferred effective amount can be determined by those skilled in the art based on various factors (e.g., through clinical trials). Such factors include, but are not limited to: pharmacokinetic parameters such as bioavailability, metabolism, half-life, etc.; severity of the tumor, patient's weights, patient's immune status, route of administration, and the like.

Typically, for the first active ingredient, a safe and effective amount is usually at least about 10 ng/kg body weight, and in most cases is no more than about 50 mg/kg body weight, preferably the dose is about 50 ng/kg body weight—about 10 mg/kg body weight. Of course, the specific dose should also take into account the administration method, the patient's health and other factors, which are all within the skill of a skilled physician.

For the second active ingredient, a safe and effective amount is usually at least about 10 ng/kg body weight, and in most cases is no more than about 50 mg/kg body weight, preferably the dose is about 50 ng/kg body weight—about 10 mg/kg body weight. Of course, the specific dose should also take into account the administration method, the patient's health and other factors, which are all within the skill of a skilled physician.

The administration method of the pharmaceutical composition of the present invention is not particularly limited, and representative examples include (but are not limited to): intravenous injection, subcutaneous injection, intramuscular injection, and the like.

Kit

The present invention provides a kit comprising:

component (1): a preparation comprising a PEGylated (PEG) interferon;

component (2): a preparation comprising a protooncogene product targeting inhibitor; and component (3): an instruction.

The preparation comprising a PEGylated (PEG) interferon includes (but is not limited to): lyophilized preparation, liquid preparation or intravenous injection.

The preparation comprising a protooncogene product targeting inhibitor includes (but is not limited to): lyophilized preparation, liquid preparation, tablets, capsules, suppositories, or intravenous injection.

In the present invention, a protein preparation is usually a lyophilized preparation or injection. Typically, a kit contains one or more (e.g., at least two) units of dosage form comprising a PEGylated (PEG) interferon and one or more (e.g., at least two) units of dosage form comprising a protooncogene product targeting inhibitor; preferably each has 4-10 units of dosage form.

As used herein, the term "unit of dosage form" refers to a composition prepared for convenience of administration in a dosage form required for a single administration, including but not limited to various solid agents (e.g., tablets), liquid agents, capsules, sustained-release agents.

The instruction of the present invention may comprise the following description: the use method of the kit is to use a unit of dosage form comprising a PEGylated (PEG) interferon and a unit of dosage form comprising a protooncogene product targeting inhibitor at the same time.

The kit of the present invention is prepared by the following steps: placing a preparation comprising a PEGylated (PEG) and a preparation comprising a protooncogene product targeting inhibitor together with the instruction, thereby forming the kit.

The preparation comprising a PEGylated (PEG) interferon preferably comprises a unit of dosage form comprising a PEGylated (PEG) interferon, and the preparation comprising a protooncogene product targeting inhibitor preferably comprises a unit of dosage form comprising a protooncogene product targeting inhibitor.

In the steps, preferably, at least one unit dosage form comprising the PEGylated (PEG) interferon and at least one unit dosage form comprising the protooncogene product targeting inhibitor, together with the instructions, are placed together to form a kit.

Beneficial Effects of the Present Invention

1. A PEGylated (PEG) and a protooncogene product targeting inhibitor (e.g. Bevacizumab (AVASTIN) or Trastuzumab (HERCEPTIN), etc.) can act synergistically in anti-tumor therapy, thereby inhibiting tumor growth more significantly.
2. The combined use of a PEGylated (PEG) interferon and a protooncogene product targeting inhibitor (e.g. Bevacizumab (AVASTIN) or Trastuzumab (HERCEPTIN), etc.) can significantly reduce the dosage of the PEGylated (PEG) interferon and can show faster and stronger anti-tumor therapeutic effects. Therefore, it can significantly reduce the side effects caused by long-term and/or high-dose use of interferons.
3. The combined use of a PEGylated (PEG) interferon and a protooncogene product targeting inhibitor (e.g. Trastuzumab (HERCEPTIN)) has shown unexpectedly excellent effects in specific tumors such as breast cancer, and even it appears the therapeutic effects of complete disappearance of a high proportion of tumor tissues. However, similar phenomena were not observed when the PEGylated (PEG) interferon or Trastuzumab (HERCEPTIN) was used alone.

The present invention will be further illustrated below with reference to the specific examples. It should be understood that these examples are only to illustrate the invention, not to limit the scope of the invention. The experimental methods with no specific conditions described in the following examples are generally performed under the conventional conditions e.g., the conditions described by Sambrook et al., Molecular Cloning: Laboratory Guide (New York: Cold Spring Harbor Laboratory Press, 1989), or according to the manufacture's instructions. Unless indicated otherwise, all percentage and parts are calculated by weight.

Reagents

In each embodiment, the PEG-interferon refers to a PEGylated (PEG) interferon α1b (Shanghai Institute of Biological Products Co., Ltd.), white lyophilized powder injection, 100 μg/bottle (0.5 ml), 100,000 IU in total (i.e., 1,000 IU/μg).

Bevacizumab (AVASTIN) (Bevacizumab injection) is a commercially available product. Trastuzumab (HERCEPTIN) is a commercially available product.

General Method

The use and welfare of laboratory animals were carried out in accordance with the regulations of the Association for the Assessment and Accreditation of Laboratory Animal Care International (AAALAC). The health status and death of the animals were monitored daily. Routine inspections included observing the effects of the test substances and drugs on animals' daily behaviors, such as behavioral activities, weight changes, and physical signs.

The indicators of tumor inhibition experiments in mice were to investigate the effect of drugs on tumor growth, and the specific indicators were T/C % or the rate of tumor growth inhibition TGI (%).

The diameter of the tumor was measured with a vernier caliper twice a week, and the formula for calculating the tumor volume (V) was: V=½xaxb2, wherein a and b represented the length and width, respectively.

$$T/C(\%)=(T-T_0)/(C-C_0)\times 100,$$

wherein, T and C were the tumor volumes at the end of the experiment; $T_0$ and $C_0$ were the tumor volumes at the beginning of the experiment.

The rate of tumor growth inhibition (TGI) (%)=100−T/C (%).

When the tumor regressed, the rate of tumor growth inhibition (TGI) (%) was $=100-(T-T_0)/T_0\times 100$ If a tumor was smaller than the initial volume, i.e., $T<T_0$ or $C<C_0$, it was defined as partial regression (PR) of the tumor; if a tumor disappeared completely, it was defined as complete regression (CR) of the tumor.

At the end of the experiment (e.g., D21), reaching the experimental endpoint, or the tumor volume reached 1,500 $mm^3$, the animals were sacrificed after $CO_2$ anesthesia, and then the tumors were dissected and photographed.

Example 1

Therapeutic effects of using PEGylated (PEG) interferon α1b for injection alone or in combination with Bevacizumab (AVASTIN) on subcutaneous transplanted tumors of human gastric cancer NCI-N87 in nude mice 1. Summary The therapeutic effects of using PEGylated (PEG) interferon α1b for injection (referred to as "PEGylated (PEG) interferon") alone or in combination with Bevacizumab (AVASTIN) on subcutaneous transplanted tumors of human gastric cancer NCI-N87 in nude mice were evaluated. PEGylated (PEG) interferon (0.1, 1, 10 mg/kg, SC, 2 times a week, 5 times in total); Bevacizumab (AVASTIN®) (10 mg/kg, IV, 2 times a week, 5 times in total); or PEGylated (PEG) interferon (1 mg/kg, SC, 2 times a week, 5 times in total) and Bevacizumab (AVASTIN®) (10 mg/kg, IV, 2 times a week, 5 times in total) in combination were used.

2. Experimental Purpose

To evaluate the therapeutic effects of using PEGylated (PEG) interferon alone or in combination with Bevacizumab (AVASTIN) on subcutaneous transplanted tumors of human gastric cancer NCI-N87 in nude mice.

3. Test Drugs 3.1 Drug Information

PEGylated (PEG) interferon α1b for injection (referred to as "PEGylated (PEG) interferon"): white lyophilized powder injection, 100 μg/bottle (0.5 ml), batch number S20170908; protected from light, sealed and stored at 2-8° C. which was produced and provided by Shanghai Institute of Biological Products Co., Ltd.

Bevacizumab (AVASTIN) (Bevacizumab injection): colorless and clear liquid, 100 mg (4 ml)/bottle; batch number H0182B03; protected from light, sealed and stored at 2-8° C., which was purchased from Roche Pharmaceuticals.

3.2 Drug Formulation

Each bottle of PEGylated (PEG) interferon was added with 120 μl of sterile water for injection at a concentration of 1 mg/ml, prepared before use, and diluted with normal saline; Bevacizumab (AVASTIN) was at a concentration of 25 mg/ml and was directly diluted with normal saline to the desired concentration.

4. Cells

Human gastric cancer NCI-N87 cells were purchased from American Type Culture Collection. NCI-N87 cells were cultured in a 10-cm culture dish by adherent culture method, and the culture conditions were RPMI 1640 medium with 10% fetal bovine serum, penicillin and streptomycin, and cultured at 37° C. in an incubator with air containing 5% $CO_2$. Cell passage was carried out 2-3 times a week, and when cells were in exponential growth phase, the cells were then digested with trypsin, collected, counted and seeded.

5. Experimental Animals

[D000521] BALB/c-Foxn1nu/Gpt mice, 4-8 weeks, 9, were purchased from Jiangsu Jicui Yaokang Biotechnology Co., Ltd. Production license number: SCXK (Su) 2018-0008; animal certificate number 201900949. Breeding environment: SPF grade.

6. Experimental Steps

Nude mice were subcutaneously (SC) inoculated with $6\times10^6$ human gastric cancer NCI-N87 cells. After the tumor grew to 100-150 $mm^3$, the animals were grouped according to tumor volume (DO). Mice were administered subcutaneously (SC) or intravenously (IV), twice a week (BIW); the administration volume was 10 mL/kg; the solvent group was administered with the same volume of "solvent" (normal saline); specific dosage and administration regimen were shown in Table 1. The tumor volumes were measured twice a week, the mice were weighed, and the data were recorded.

7. Statistical Analysis

Two-tailed Student's t-test was used to compare tumor volumes between the two groups, and P<0.05 was defined as a statistically significant difference.

8. Results

Figure 2:
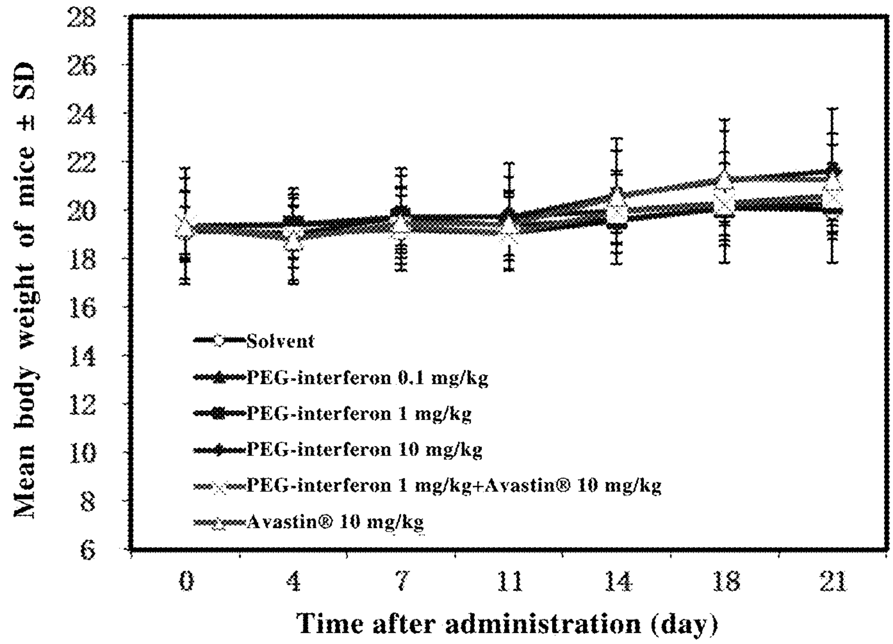
FIG. 2 shows the therapeutic effects of using PEGylated (PEG) interferon or Bevacizumab (AVASTIN) alone or in combination on the body weights of NCI-N87 tumor-bearing nude mice.
Figure 3:
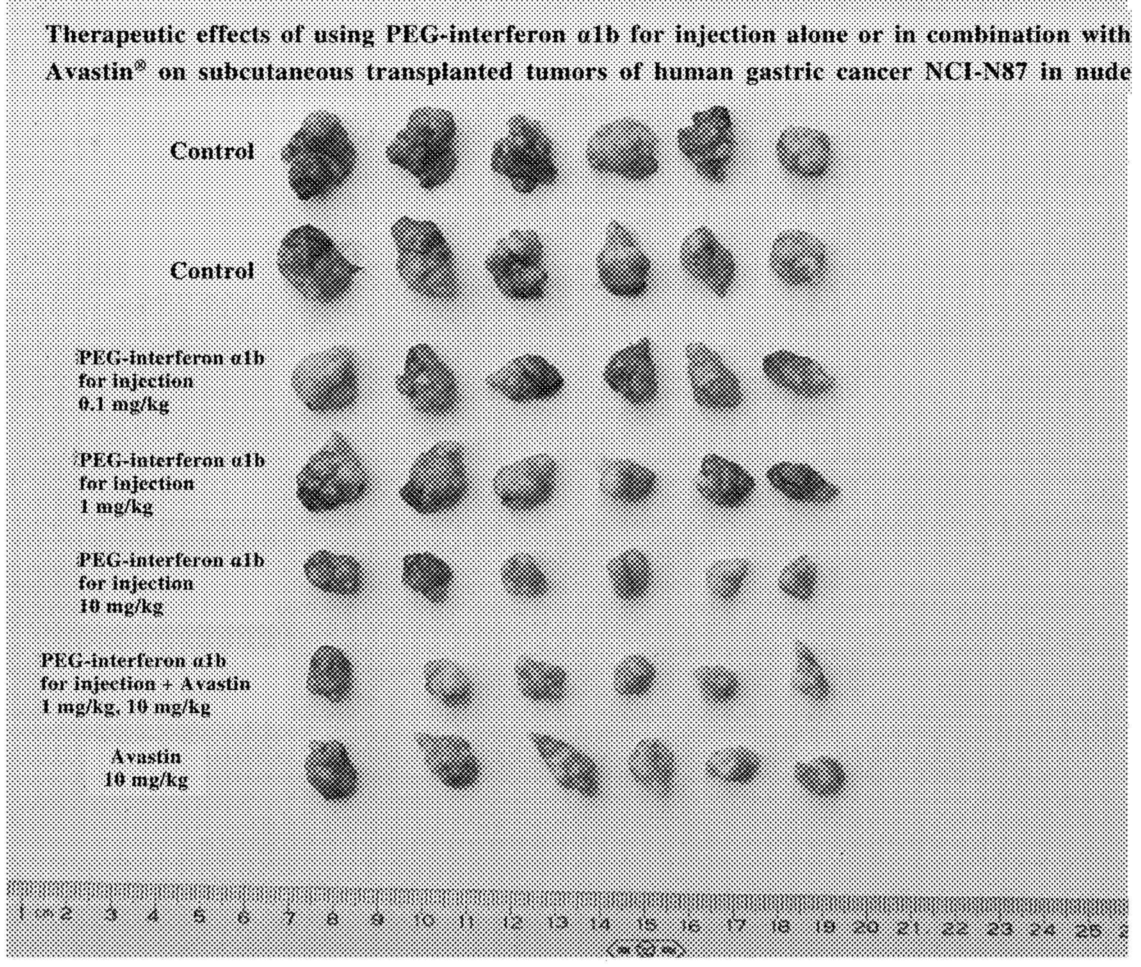
FIG. 3 shows the therapeutic effects of using the PEGylated (PEG) interferon or Bevacizumab (AVASTIN) alone or in combination on subcutaneous transplanted tumors of human gastric cancer NCI-N87 in nude mice.

The results were shown in Table 1 and FIGS. 1, 2 and 3.

TABLE 1

Therapeutic effects of using PEGylated (PEG) interferon or Avastin alone or in combination on subcutaneous transplanted tumors of human gastric cancer NCI-N87 in nude mice.

| Groups | Administration | Routes | Mean tumor volume ($mm^3$) D 0 SEM | Mean tumor volume ($mm^3$) D 21 SEM | % T/C D 21 | Tumor inhibition rate % D 21 | P value D 21 | Per group Number of animals |
|---|---|---|---|---|---|---|---|---|
| Solvent | D 0, 3, 7, 10, 14, 17 | SC | 113.2 ± 2.8 | 986.9 ± 54.1 | — | — | — | 12 |
| PEGylated (PEG) interferon 0.1 mg/kg | D 0, 3, 7, 10, 14, 17 | SC | 112.7 ± 3.9 | 817.1 ± 84.9 | 81 | 19 | 0.103 | 6 |
| PEGylated (PEG) interferon 1 mg/kg | D 0, 3, 7, 10, 14, 17 | SC | 117.4 ± 2.8 | 712.4 ± 68.4 | 68 | 32 | ** 0.008 | 6 |
| PEGylated (PEG) interferon 10 mg/kg | D 0, 3, 7, 10, 14, 17 | SC | 112.3 ± 2.3 | 506.1 ± 33.0 | 45 | 55 | 0.000 | 6 |
| PEGylated (PEG) interferon 1 mg/kg + Avastin 10 mg/kg | D 0, 3, 7, 10, 14, 17/ D 0, 3, 7, 10, 14, 17 | SC/IV | 113.5 ± 2.9 | 399.9 ± 38.9 | 33 | 67 | 0.000 | 6 |
| Avastin 10 mg/kg | D 0, 3, 7, 10, 14, 17 | IV | 115.7 ± 2.7 | 561.1 ± 53.4 | 51 | 49 | * 0.000 | 6 |

D 0: time of first administration;
the first dose of Avastin was doubled;
SC: subcutaneous injection;
IV: intravenous injection;
P value referred to the comparison with solvent;
*P < 0.05,
**P < 0.01, compared with the dose group PEGylated (PEG) 1 mg/kg + Avastin 10 mg/kg.

PEGylated (PEG) interferon (0.1, 1, 10 mg/kg, SC, twice a week, 6 times in total) dose-dependently inhibited the growth of subcutaneous transplanted tumors of human gastric cancer NCI-N87 in nude mice, and the tumor inhibition rates were 19%, 32% and 55%, respectively. The tumor inhibition rate of Bevacizumab (AVASTIN®) (10 mg/kg, IV, 2 times a week, 6 times in total) on NCI-N87 subcutaneous transplanted tumors was 49%.

When PEGylated (PEG) interferon (1 mg/kg, SC, 2 times a week, 6 times in total) was used in combination with Bevacizumab (AVASTIN®) (10 mg/kg, IV, 2 times a week, 6 times in total), the tumor inhibition rate of NCI-N87 was significantly increased to 67% ($P<0.05$, compared with monotherapy), showing synergistic inhibition.

In addition, tumor-bearing mice showed good tolerance to the drugs when they were used in combination, and no symptoms such as weight loss occurred. As shown in FIG. 2, the body weights of the mice in the combination group of PEGylated (PEG) interferon α1b (1 mg/kg, SC, 2 times a week, 6 times in total) and Bevacizumab (AVASTIN) (10 mg/kg, IV, 2 times a week, 6 times in total) were basically indistinguishable from the body weights of the mice in the PEG-interferon (1 mg/kg) alone group and the Bevacizumab (AVASTIN) (10 mg/kg) alone group.

The above experimental results showed that PEGylated (PEG) interferon α1b combined with Bevacizumab (AVASTIN) had a significant synergistic inhibitory effect on the subcutaneous transplanted tumors of human gastric cancer NCI-N87 in nude mice, and the tumor-bearing mice had good drug tolerance, side effects decreased, and no symptoms such as weight loss occurred.

9. Conclusion

As shown in FIGS. 1, 2 and 3, PEGylated (PEG) interferon (0.1, 1, 10 mg/kg, SC, 2 times a week, 6 times in total) dose-dependently inhibited the growth of subcutaneous transplanted tumors of human gastric cancer NCI-N87 in nude mice. Bevacizumab (AVASTIN®) (10 mg/kg, IV, 2 times a week, 6 times in total) was also effective on NCI-N87 subcutaneous transplanted tumors.

When used in combination, PEGylated (PEG) interferon had a significant synergistic effect on subcutaneous transplanted tumors in NCI-N87 nude mice treated with Bevacizumab (AVASTIN) ($P<0.05$, compared with PEGylated (PEG) interferon or Bevacizumab (AVASTIN) monotherapy). In addition, tumor-bearing mice showed good tolerance to the drugs when used in combination without increased toxicity.

Example 2

Therapeutic Effects of Using PEGylated (PEG) Interferon α1b for Injection Alone or in Combination with Bevacizumab (AVASTIN) on Subcutaneous Transplanted Tumors of Human Liver Cancer Huh-7 in Nude Mice 1. Summary The therapeutic effects of using PEGylated (PEG) interferon α1b for injection (referred to as "PEGylated (PEG) interferon") alone or in combination with Bevacizumab (AVASTIN) on subcutaneous transplanted tumors of human liver cancer Huh-7 in nude mice were evaluated. PEGylated (PEG) interferon (0.1, 1, 10 mg/kg, SC, 2 times a week, 5 times in total); Bevacizumab (AVASTIN®) (10 mg/kg, IV, 2 times a week, 5 times in total); or PEGylated (PEG) interferon (1 mg/kg, SC, 2 times a week, 5 times in total) and Bevacizumab (AVASTIN®) (10 mg/kg, IV, 2 times a week, 5 times in total) in combination were used in combination.

2. Experimental Purpose

To evaluate the therapeutic effects of using PEGylated (PEG) interferon alone or in combination with Bevacizumab (AVASTIN) on subcutaneous transplanted tumors of human liver cancer Huh-7 in nude mice.

3. Test Drugs 3.1 Drug Information

PEGylated (PEG) interferon α1b for injection (referred to as "PEGylated (PEG) interferon"): the same as that in Example 1.

Bevacizumab (AVASTIN) (Bevacizumab injection): the same as that in Example 1.

3.2 Drug Formulation

Each bottle of PEGylated (PEG) interferon was added with 120 μl of sterile water for injection at a concentration of 1 mg/ml, prepared before use, and diluted with normal saline; Bevacizumab (AVASTIN) was at a concentration of 25 mg/ml and was directly diluted with normal saline to the desired concentration.

4. Cells

Human liver cancer Huh-7 cells were purchased from the Chinese Academy of Sciences Cell Bank. Huh-7 cells were cultured in a 10-cm culture dish by adherent culture method, and the culture conditions were RPMI 1640 medium with 10% fetal bovine serum, penicillin and streptomycin, and cultured at 37° C. in an incubator with air containing 5% $CO_2$. Cell passage was carried out 2-3 times a week, and when cells were in exponential growth phase, the cells were then digested with trypsin, collected, counted and seeded.

5. Experimental Animals

[D000521] BALB/c-Foxn1nu/Nju mice, 6-7 weeks, 9, were purchased from Jiangsu Jicui Yaokang Biotechnology Co., Ltd. Production license number: SCXK (Su) 2018-0008; animal certificate number 201900949. Breeding environment: SPF grade.

6. Experimental Steps

Nude mice were subcutaneously inoculated with $6\times10^6$ human liver cancer Huh-7 cells. After the tumor grew to 100-150 $mm^3$, the animals were grouped according to tumor volume (DO). Mice were administered subcutaneously (SC) or intravenously (IV), twice a week (BIW); the administration volume was 10 mL/kg; the solvent group was administered with the same volume of "solvent" (normal saline); specific dosage and administration regimen were shown in Table 2. The tumor volumes were measured twice a week, the mice were weighed, and the data were recorded.

7. Statistical Analysis

Two-tailed Student's t-test was used to compare tumor volumes between the two groups, and P<0.05 was defined as a statistically significant difference.

8. Results

Figure 4:
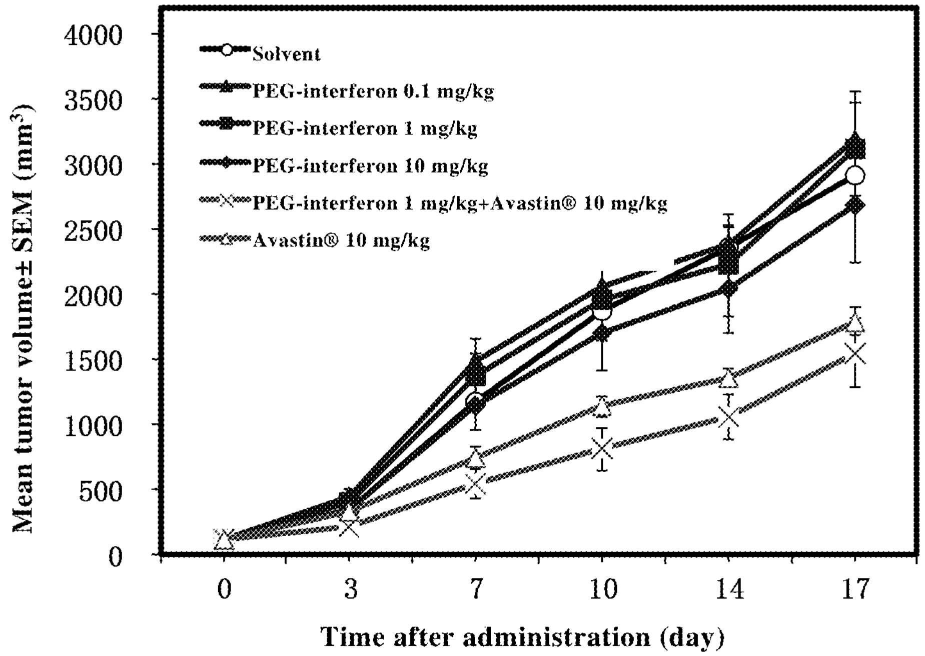
FIG. 4 shows the therapeutic effects of using PEGylated (PEG) interferon or Bevacizumab (AVASTIN) alone or in combination on subcutaneous transplanted tumors of human liver cancer Huh-7 in nude mice.
Figure 5:
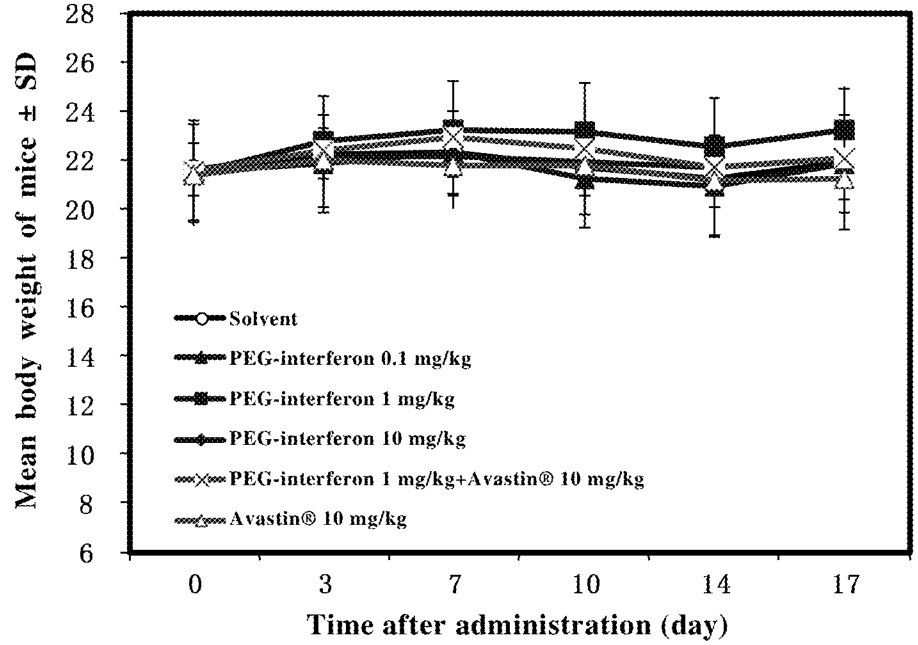
FIG. 5 shows the therapeutic effects of using PEGylated (PEG) interferon or Bevacizumab (AVASTIN) alone or in combination on the body weights of Huh-7 tumor-bearing nude mice.
Figure 6:
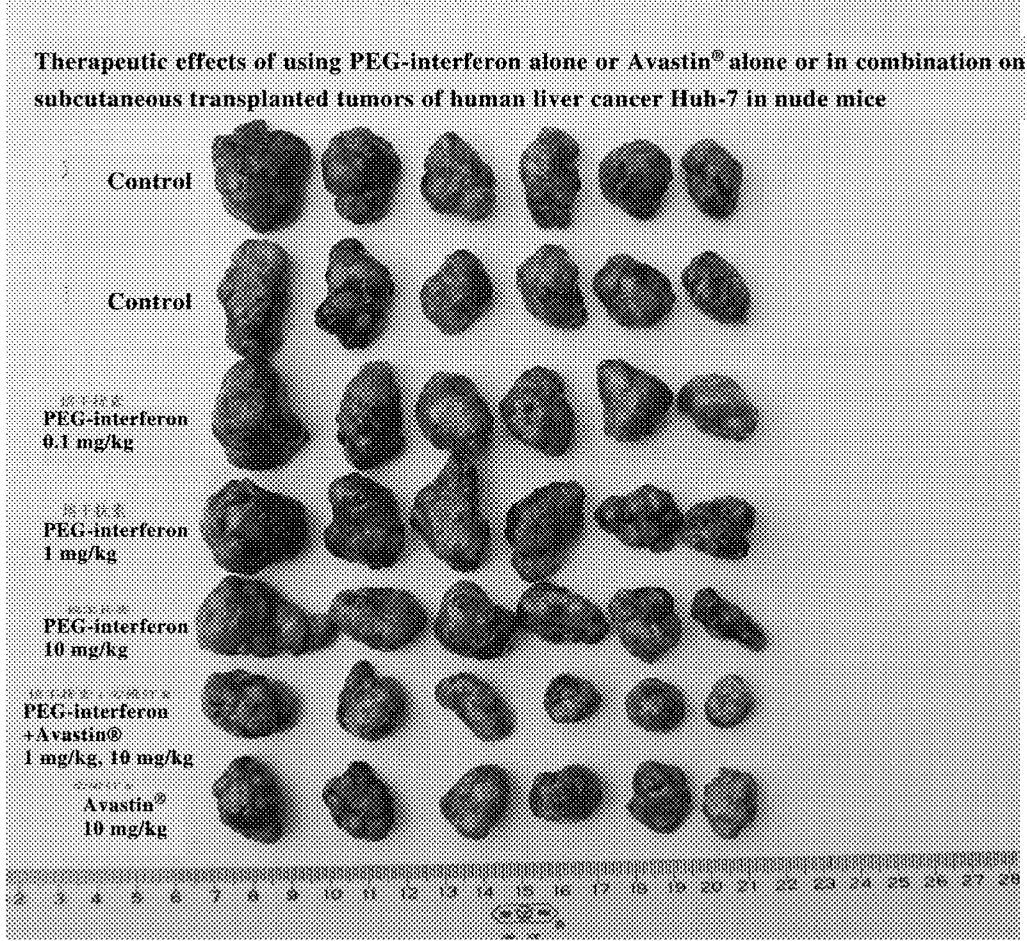
FIG. 6 shows the therapeutic effects of using PEGylated (PEG) interferon or Bevacizumab (AVASTIN) alone or in combination on subcutaneous transplanted tumors of human liver cancer Huh-7 in nude mice.

The results were shown in Table 2 and FIGS. 4, 5 and 6.

9. Conclusion

As shown in FIGS. 4, 5 and 6, PEGylated (PEG) interferon (0.1, 1, 10 mg/kg, SC, 2 times a week, 5 times in total) had no significant inhibitory effect on the growth of subcutaneous transplanted tumors of human liver cancer Huh-7 in nude mice. Bevacizumab (AVASTIN®) (10 mg/kg, IV, 2 times a week, 5 times in total) was effective on Huh-7 subcutaneous transplanted tumors.

TABLE 2

Therapeutic effects of using PEGylated (PEG) interferon or Avastin alone or in combination on subcutaneous transplanted tumors of human liver cancer Huh-7 in nude mice.

| Groups | Administration | Routes | Mean tumor volume ($mm^3$) D 0 SEM | Mean tumor volume ($mm^3$) D 17 SEM | % T/C D 17 | Tumor inhibition rate % D 17 | P value D 17 | Per group Number of animals |
|---|---|---|---|---|---|---|---|---|
| Solvent | D 0, 3, 7, 10, 14 | SC | 119.5 ± 1.3 | 2916.2 ± 164.1 | — | — | — | 12 |
| PEGylated (PEG) interferon 0.1 mg/kg | D 0, 3, 7, 10, 14 | SC | 117.7 ± 2.0 | 3188.0 ± 282.5 | 110 | −10 | 0.383 | 6 |
| PEGylated (PEG) interferon 1 mg/kg | D 0, 3, 7, 10, 14 | SC | 119.8 ± 2.6 | 3110.6 ± 438.0 | 107 | −7 | * 0.618 | 6 |
| PEGylated (PEG) interferon 10 mg/kg | D 0, 3, 7, 10, 14 | SC | 123.8 ± 1.9 | 2681.9 ± 435.7 | 91 | 9 | 0.539 | 6 |
| PEGylated (PEG) interferon 1 mg/kg + Avastin 10 mg/kg | D 0, 3, 7, 10, 14/ D 0, 3, 7, 10, 14 | SC/IV | 120.5 ± 1.7 | 1549.1 ± 260.9 | 51 | 49 | 0.000 | 6 |
| Avastin 10 mg/kg | D 0, 3, 7, 10, 14 | IV | 122.7 ± 1.8 | 1791.6 ± 105.7 | 60 | 40 | 0.000 | 6 |

D 0: time of first administration;
the first dose of Avastin was doubled;
SC: subcutaneous injection;
IV: intravenous injection;
P value referred to the comparison with solvent;
*P < 0.05, compared with the dose group PEGylated (PEG) 1 mg/kg + Avastin 10 mg/kg.

PEGylated (PEG) interferon (0.1, 1, 10 mg/kg, SC, twice a week, 5 times in total) dose-dependently inhibited the growth of subcutaneous transplanted tumor of human liver cancer Huh-7 in nude mice, and the tumor inhibition rates were-10%,-7% and 9%, respectively. The tumor inhibition rate of Bevacizumab (AVASTIN®) (10 mg/kg, IV, 2 times a week, 5 times in total) on Huh-7 subcutaneous transplanted tumors was 40%.

When PEGylated (PEG) interferon (1 mg/kg, SC, 2 times a week, 5 times in total) was used in combination with Bevacizumab (AVASTIN®) (10 mg/kg, IV, 2 times a week, 5 times in total), the tumor inhibition rate of Huh-7 was increased to 49%. PEGylated (PEG) interferon had certain synergistic effect on subcutaneous transplanted tumors of human liver cancer Huh-7 in nude mice treated with Bevacizumab (AVASTIN).

In addition, tumor-bearing mice showed good tolerance to the drugs when they were used in combination, and no symptoms such as weight loss occurred. As shown in FIG. 5, the body weights of the mice in the combination group of PEGylated (PEG) interferon α1b (1 mg/kg, SC, 2 times a week, 6 times in total) and Bevacizumab (AVASTIN) (10 mg/kg, IV, 2 times a week, 6 times in total) were basically indistinguishable from the body weights of the mice in the PEG-interferon (1 mg/kg) alone group and the Bevacizumab (AVASTIN) (10 mg/kg) alone group. Moreover, the body weights of the combination group were higher than those of Bevacizumab (AVASTIN) (10 mg/kg) alone group, which suggested that the side effects of Bevacizumab (AVASTIN) administration could be further reduced when it was used in combination.

When used in combination, PEGylated (PEG) interferon had a synergistic effect on subcutaneous transplanted tumors of human liver cancer Huh-7 in nude mice treated with Bevacizumab (AVASTIN). In addition, tumor-bearing mice showed good tolerance to the drugs when used in combination without increased toxicity.

Example 3

Therapeutic Effects of Using PEGylated (PEG) Interferon α1b for Injection Alone or in Combination with Trastuzumab (HERCEPTIN) on Subcutaneous Transplanted Tumors of Human Breast Cancer BT-474 in Nude Mice 1. Summary The therapeutic effects of using PEGylated (PEG) interferon α1b for injection (referred to as "PEGylated (PEG) interferon") alone or in combination with Trastuzumab (HERCEPTIN) on subcutaneous transplanted tumors of human breast cancer BT-474 in nude mice were evaluated. PEGylated (PEG) interferon (0.1, 1, 10 mg/kg, SC, 2 times a week, 6 times in total); Trastuzumab (HERCEPTIN®) (5 mg/kg, IV, 2 times a week, 6 times in total); or PEGylated (PEG) interferon (1 mg/kg, SC, 2 times a week, 6 times in total) and Trastuzumab (HERCEPTIN®) (5 mg/kg, IV, 2 times a week, 6 times in total) in combination were used.

2. Experimental Purpose

To evaluate the therapeutic effects of using PEGylated (PEG) interferon alone or in combination with Trastuzumab (HERCEPTIN) on subcutaneous transplanted tumors of human breast cancer BT-474 in nude mice.

3. Test Drugs 3.1 Drug Information

PEGylated (PEG) interferon α1b for injection (referred to as "PEGylated (PEG) interferon"): the same as that in Example 1.

Trastuzumab (HERCEPTIN) (Trastuzumab injection), loose lumps between white and light yellow, spec 440 mg (20 ml)/bottle, product batch number/diluent batch number N3886/B3083; production date 20170220 (product)/20161118 (diluent), valid until 20200219. Protected from light and stored at 2-8° C.

3.2 Suppliers

PEGylated (PEG) interferon was provided by Shanghai Institute of Biological Products Co., Ltd; and Trastuzumab (HERCEPTIN) was purchased from Roche Pharmaceuticals.

3.3 Drug Formulation

PEGylated (PEG) interferon: each bottle of PEGylated (PEG) interferon was added with 120 μl of sterile water for injection at a concentration of 1 mg/ml, prepared before use; diluted with normal saline;

Trastuzumab (HERCEPTIN): it was first reconstituted with the solvent provided by the original manufacturer, and it became colorless to light yellow after dissolving, clear to a slightly opalescent solution, and the concentration after reconstitution was 21 mg/ml; then it was immediately sub-packaged and frozen at −70~80° C. It was diluted with normal saline to the desired concentration before use.

4. Cells

Human breast cancer BT-474 cells were purchased from American Type Culture Collection. BT-474 cells were cultured in a 10-cm culture dish by adherent culture method, and the culture conditions were DMEM medium (Gibco) with 10% fetal bovine serum (Gibco), penicillin and streptomycin, and cultured at 37° C. in an incubator (Thermo) with air containing 5% $CO_2$. Cell passage was carried out 2-3 times a week, and when cells were in exponential growth phase, the cells were then digested with trypsin, collected, counted and seeded.

5. Experimental Animals

[D000521] BALB/cJGpt-Foxn1nu/Gpt mice, 5 weeks, 9, purchased from Jiangsu Jicui Yaokang Biotechnology Co., Ltd. Production license number: SCXK (Su) 2018-0008; animal certificate number 201901062. Breeding environment: SPF grade.

6. Experimental Steps

Nude mice were subcutaneously inoculated with $1\times10^7$ human breast cancer BT-474 cells. After the tumor grew to 100-150 $mm^3$, the animals were grouped according to tumor volume (DO). Mice were administered subcutaneously (SC) or intravenously (IV), twice a week (BIW); the administration volume was 10 mL/kg; the solvent group was administered with the same volume of "solvent" (normal saline); specific dosage and administration regimen were shown in Table 3. The tumor volumes were measured twice a week, the mice were weighed, and the data were recorded.

7. Statistical Analysis

Two-tailed Student's t-test was used to compare tumor volumes between the two groups, and P<0.05 was defined as a statistically significant difference.

8. Results

Figure 7:
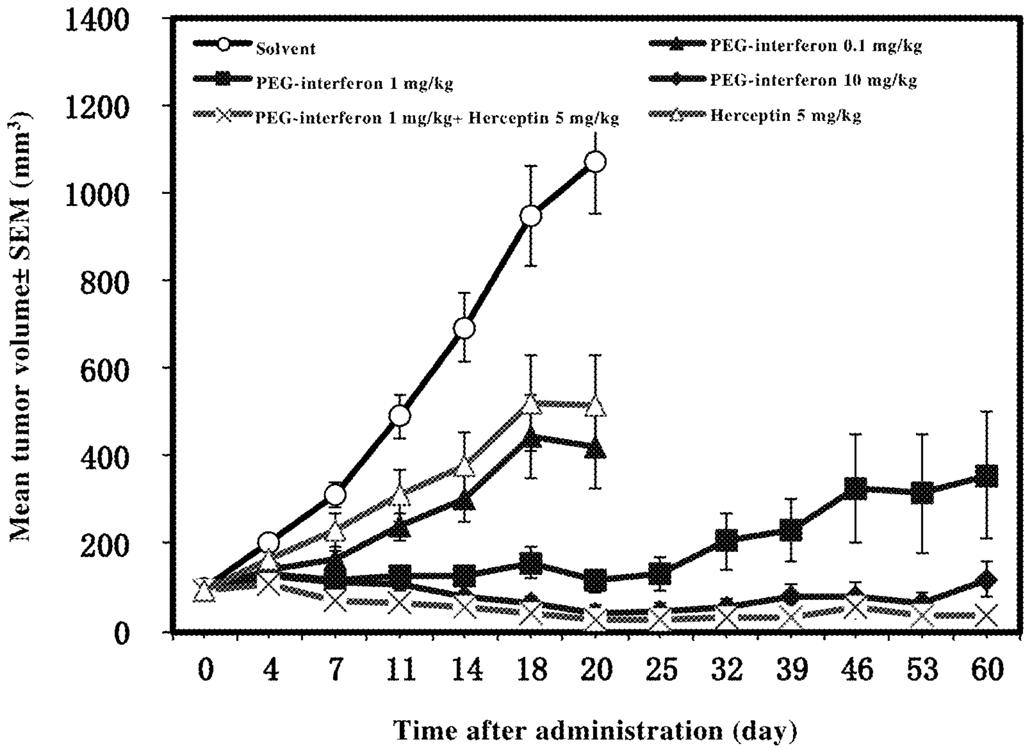
FIG. 7 shows the therapeutic effects of using PEGylated (PEG) interferon or Trastuzumab (HERCEPTIN) alone or in combination on subcutaneous transplanted tumors of human breast cancer BT-474 in nude mice.
Figure 8:
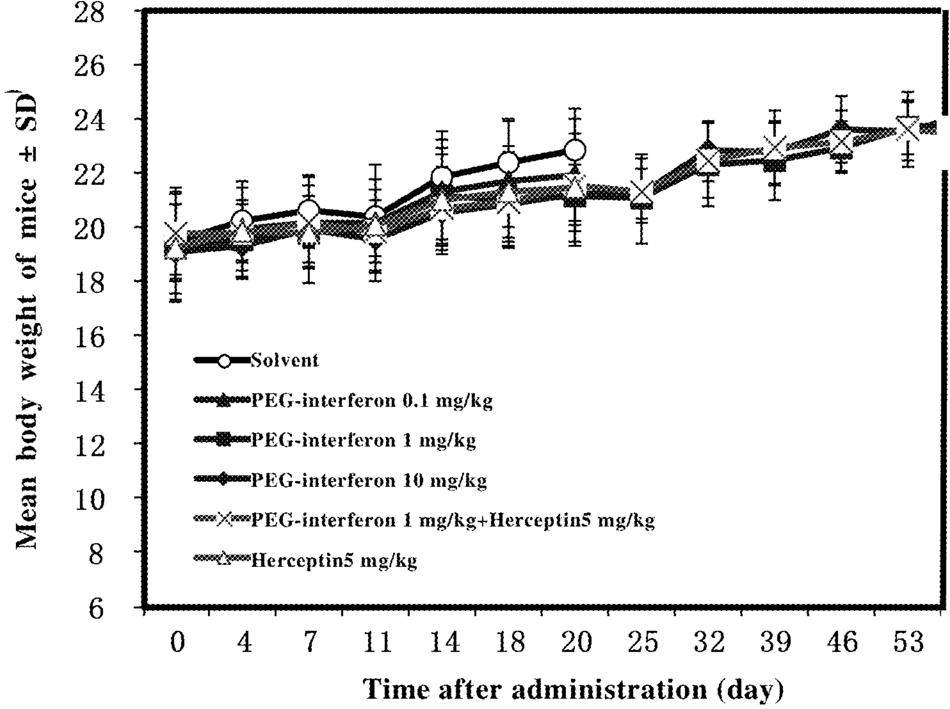
FIG. 8 shows the therapeutic effects of using PEGylated (PEG) interferon or Trastuzumab (HERCEPTIN) alone or in combination on the body weights of BT-474 tumor-bearing nude mice.
Figure 9:
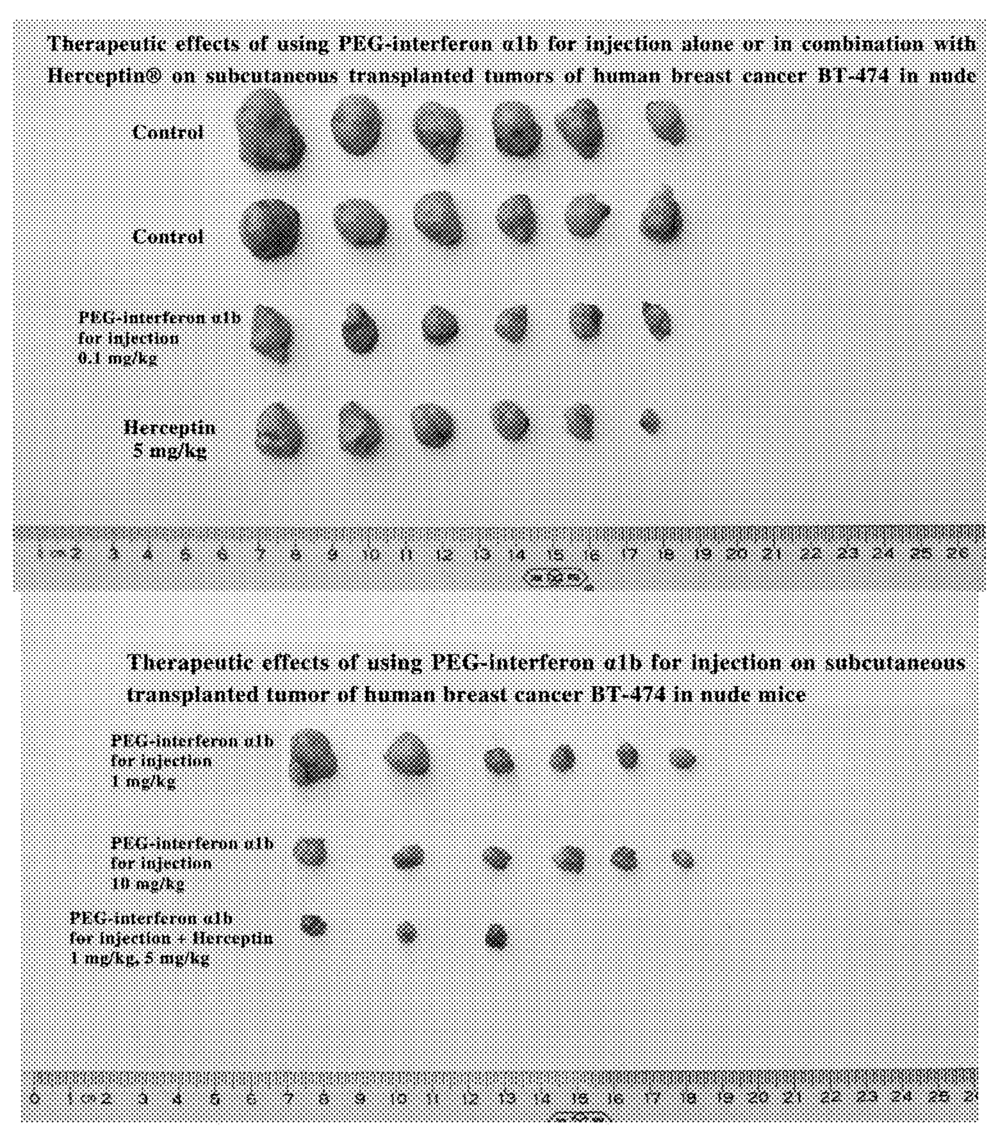
FIG. 9 shows the therapeutic effects of using PEGylated (PEG) interferon or Trastuzumab (HERCEPTIN) alone or in combination on subcutaneous transplanted tumors of human breast cancer BT-474 in nude mice. Above Figure: D20; below figure: D60.

The results were shown in Table 3 and FIGS. 7, 8 and 9.

TABLE 3

Therapeutic effects of using PEGylated (PEG) interferon or Herceptin alone or in combination on subcutaneous transplanted tumors of human breast cancer BT-474 in nude mice.

| Groups | Administration | Routes | Mean tumor volume ($mm^3$) D 0 SEM | Mean tumor volume ($mm^3$) D 20 SEM | % T/C D 20 | Tumor inhibition rate % D 20 | P value D 20 | Per group Number of animals |
|---|---|---|---|---|---|---|---|---|
| Solvent | D 0, 3, 7, 10, 14, 17 | SC | 96.5 ± 2.5 | 1071.9 ± 119.9 | — | — | — | 12 |
| PEGylated (PEG) interferon 0.1 mg/kg | D 0, 3, 7, 10, 14, 17 | SC | 91.2 ± 1.3 | 422.2 ± 97.0 | 34 | 66 | 0.003 | 6 |
| PEGylated (PEG) interferon 1 mg/kg | D 0, 3, 7, 10, 14, 17 | SC | 94.1 ± 4.3 | 115.7 ± 26.1 | 2 | 98 | 0.000 | 6 |
| PEGylated (PEG) interferon 10 mg/kg | D 0, 3, 7, 10, 14, 17 | SC | 94.8 ± 4.2 | 41.4 ± 15.7 | −56 | 156 | 0.000 | 6 |
| PEGylated (PEG) interferon 1 mg/kg + Herceptin 5 mg/kg | D 0, 3, 7, 10, 14, 17/ D 0, 3, 7, 10, 14, 17 | SC/IV | 92.3 ± 2.3 | 27.8 ± 12.5 | −70 | 170 | 0.000 | 6 |
| Herceptin 5 mg/kg | D 0, 3, 7, 10, 14, 17 | IV | 93.6 ± 2.4 | 514.2 ± 113.4 | 43 | 57 | 0.009 | 6 |

D 0: time of first administration;
the first dose of Herceptin was doubled;
SC: subcutaneous injection;
IV: intravenous injection;
P value referred to the comparison with solvent;
**P < 0.01, compared with the dose group PEGylated (PEG) 1 mg/kg + Herceptin 5 mg/kg.

PEGylated (PEG) interferon (0.1, 1, 10 mg/kg, SC, twice a week, 6 times in total) dose-dependently inhibited the growth of subcutaneous transplanted tumors of human breast cancer BT-474 in nude mice, and the tumor inhibition rates were 66%, 98% and 156%, respectively, 3/6 of tumors regressed partially in the 1 mg/kg group, 4/6 of tumors regressed partially and 2/6 of tumors regressed completely in the 10 mg/kg group (D20), and by the end of the experiment (D60), 4/6 of tumors still regressed partially in the 10 mg/kg group. The tumor inhibition rate of Trastuzumab (HERCEPTIN®) (5 mg/kg, IV, 2 times a week, 6 times in total) on BT-474 subcutaneous transplanted tumors was 57% (D20).

When PEGylated (PEG) interferon (1 mg/kg, SC, 2 times a week, 6 times in total) was used in combination with Trastuzumab (HERCEPTIN®) (5 mg/kg, IV, 2 times a week, 6 times in total), the tumor inhibition rate of BT-474 was much very significantly increased to 170% ($P<0.01$, compared with monotherapy), with 3/6 of tumors regressed partially and 3/6 of tumors regressed completely (D20); by the end of the experiment (D60), 3/6 of tumors still regressed partially and 3/6 of tumors regressed completely. This showed that PEGylated (PEG) interferon combined with Trastuzumab (HERCEPTIN) had a very significant synergistic effect in the treatment of subcutaneous transplanted tumors of human breast cancer BT-474 in nude mice, and even achieved the therapeutic effects of partial or complete regression.

In addition, tumor-bearing mice showed good tolerance to the drugs when they were used in combination, and no symptoms such as weight loss occurred. Especially as shown in FIG. 8, the body weights of the mice in the combination group of PEGylated (PEG) interferon α1b (1 mg/kg, SC, 2 times a week, 6 times in total) and Trastuzumab (HERCEPTIN®) (5 mg/kg, IV, 2 times a week, 6 times in total) were basically indistinguishable from the body weights of the mice in the PEG-interferon alone group and the Trastuzumab (HERCEPTIN) alone group.

9. Conclusion

As shown in FIGS. 7, 8 and 9, PEGylated (PEG) interferon (0.1, 1, 10 mg/kg, SC, 2 times a week, 6 times in total) dose-dependently inhibited the growth of subcutaneous transplanted tumors of human breast cancer BT-474 in nude mice, causing partial or complete regression of the tumor. Trastuzumab (HERCEPTIN®) (5 mg/kg, IV, 2 times a week, 6 times in total) was also effective on BT-474 subcutaneous transplanted tumors.

When used in combination, PEGylated (PEG) interferon (1 mg/kg, SC, 2 times a week, 6 times in total) and Trastuzumab (HERCEPTIN®) (5 mg/kg, IV, 2 times a week, 6 times in total) had a significant synergistic effect on the therapeutic effects of BT-474 tumors ($P<0.05$, compared with monotherapy). In addition, tumor-bearing mice showed good tolerance to the drugs when used in combination without increased toxicity.

Example 4

Inhibitory Effects of PEGylated (PEG) Interferon on Tumor Cell Lines In Vitro Sulfonyl rhodamine B protein staining method (SRB method) was used to evaluate the effects of using PEG-interferon alone or in combination with other drugs on the proliferation of tumor cells in vitro.

A certain number of cells in logarithmic growth phase were seeded in 96-well culture plates. After 24 hours of adherent growth, different concentrations (final concentrations of 1, 3, 10, 30, 100, 300, 1,000, 3,000, 10,000 nM) of drugs were added. After 120 hours of drug action, cells were fixed with trichloroacetic acid. Then stained with SRB solution; finally, Tris solution was added to dissolve SRB, and OD value was measured at a wavelength of 510 nm by a microplate reader. Cell growth inhibition rate was calculated by the following formula: inhibition rate=(OD value of control hole-OD value of dosing hole)/OD value of control hole×100%.

The results were shown in Table 4.

TABLE 4

In vitro inhibition rate of PEGylated (PEG) interferon on different tumor cell lines

| Tumor types | Tumor cell lines | Inhibition rate (%)@100 μg/mL |
|---|---|---|
| Breast cancer | MCF-7 | 24.2 |
| | BT474 | 19.6 |
| | HCC1806 | 32.6 |
| Lung cancer | NCI-H292 | 41.5 |
| | A549 | 33.7 |
| Gastric cancer | HGC27 | 52.3 |
| | AGS | 44.0 |
| | N87 | 32.5 |
| Liver cancer | HepG2 | 20.2 |
| | Hep3B | 58.4 |
| | Huh-7 | 29.3 |

Example 5

In Vitro Synergistic Inhibitory Effect of PEGylated (PEG) Interferon and Trastuzumab (HERCEPTIN) on Tumor Cell Lines The method of Example 4 was repeated except that different doses of PEG-interferon (monotherapy group 1), Trastuzumab (HERCEPTIN) (monotherapy group 2), and PEG-interferon+Trastuzumab (HERCEPTIN) (combination group) as shown in Table 5 were used. Breast cancer cells BT474 were used, and the corresponding inhibition rate (%) was calculated.

TABLE 5

| | Drug dosage | | | | | | |
|---|---|---|---|---|---|---|---|
| | 1 | 2 | 3 | 4 | 5 | 6 | 7 |
| PEG-interferon (μg/ml) | 9.38 | 18.75 | 37.50 | 75.00 | 150.00 | 300.00 | 600.00 |
| Trastuzumab (HERCEPTIN) (μg/ml) | 0.05 | 0.09 | 0.19 | 0.38 | 0.75 | 1.50 | 3.00 |
| PEG-interferon (μg/ml) + Trastuzumab (HERCEPTIN) (μg/ml) | 9.38 + 0.05 | 18.75 + 0.09 | 37.50 + 0.19 | 75.00 + 0.38 | 150.00 + 0.75 | 300.00 + 1.50 | 600.00 + 3.00 |

Note:
In the PEG-interferon, the weight ratio of IFN-α1b to PEG was about 1:1, and therefore the amount of IFN-α1b in 600 μg PEG-interferon was 300 μg (about 300,000 IU in total), and the rest may be deduced by analogy.

Figure 10:
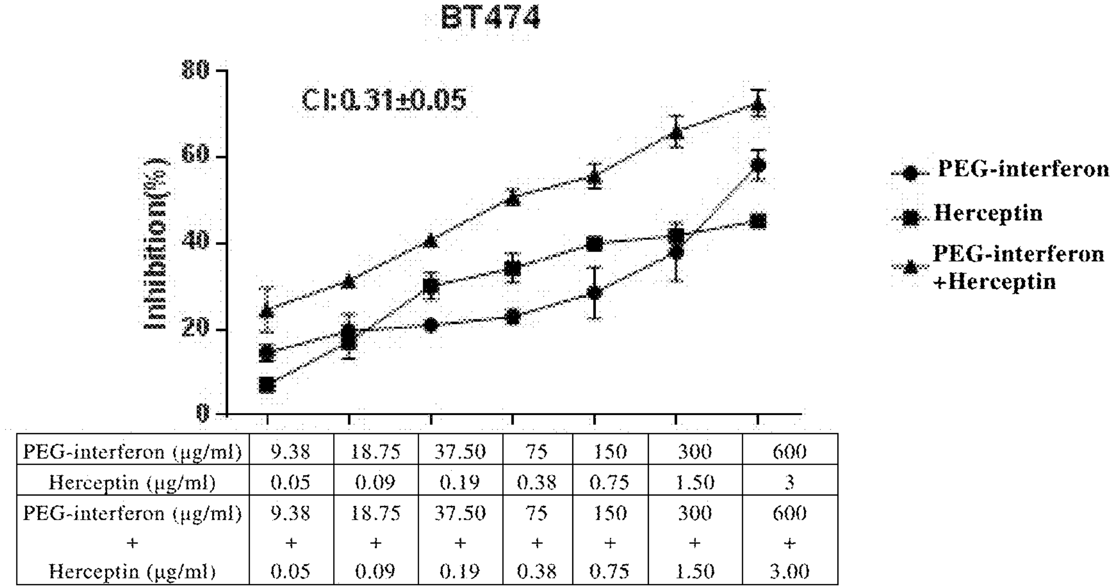
FIG. 10 shows that a combination of PEG-interferon and Trastuzumab (HERCEPTIN) has a synergistic inhibitory activity on the proliferation of human breast cancer BT-474 cells cultured in vitro, and the inhibitory effect is significantly improved. The combination index (CI value) is 0.31, indicating a synergistic effect.

As shown in FIG. 10, the results showed that the combination use of PEG-interferon and Trastuzumab (HERCEPTIN) had synergistic inhibitory activity on the proliferation of human breast cancer BT-474 cells cultured in vitro, and the inhibitory effects were significantly improved. The combination index (CI value) was 0.31, indicating a synergistic effect.

Specifically, when used in combination, when the concentration of PEG-interferon was about 9.38-600 μg/ml and the concentration of Trastuzumab (HERCEPTIN) was 0.05-3 μg/ml, a clear synergistic inhibitory effect could be observed. For example, the inhibition rate of the combination of 150 μg/ml PEG-interferon+0.75 μg/ml Trastuzumab (HERCEPTIN) was significantly higher than that of 300 μg/ml PEG-interferon alone or that of 1.5 μg/ml Trastuzumab (HERCEPTIN) alone.

DISCUSSION

Interferon is a kind of highly active protein molecules with broad-spectrum antiviral proliferation activity, antitumor activity, immunomodulatory activity and so on. In the field of tumor therapy, ordinary interferons have been approved by the US FDA and European EMA for the treatment of hairy cell leukemia, chronic myeloid leukemia, renal cancer, Kaposi's sarcoma, melanoma, follicular lymphoma, multiple myeloma, cervical intraepithelial neoplasia (Elena Garcia-Martinez, etc. Trial Watch: Immunostimulation with recombinant cytokines for cancer therapy, ONCOIMMUNOLOGY, 2018, VOL. 7, NO. 6: e1433982, 16 pages; Xiang Chen et al., Clinical research progress of immunotherapy for renal cancer, CHINESE JOURNAL OF UROLOGY, 2017 VOL. 38 NO. 9:717-720). Besides, interferon also has certain curative effects in the treatment of lung cancer, digestive tract cancer, prostate cancer, head and neck squamous cell carcinoma and other tumors.

Although ordinary interferons are safe and effective preparations, there are still some problems, especially serious side effects. The ordinary interferons currently used in clinical practice are easy to be filtered by the glomerulus due to their small molecular weights (below 20 kDa), resulting in a half-life of only 1.5-2 hours in the human body. In order to achieve the desired therapeutic effect, a general clinical treatment of ordinary interferons uses high doses and multiple injections, which leads to poor patient compliance and is prone to side effects.

Taking melanoma as an example, it is necessary to subcutaneously inject ordinary interferons 20 million IU/m$^2$ (approximately equal to 400 μg/person) for 5 days/week, then 10 million IU/m$^2$ (approximately 200 μg/person) after 1 month, and maintain the treatment 3 times a week for 48 weeks. The treatment can prolong the survival of patients, but the adverse reactions of administering high-dose ordinary interferons are very obvious. At least 50% of patients need to delay or reduce the dose, so it can only be used for high-risk patients.

The adverse reactions of ordinary interferon α in the human body are systemic (Xue-lin, Cao, Mechanism of interferon adverse reactions, BIOMEDICAL ENGINEERING AND CLINICAL MEDICINE, 2010, VOL. 14, NO. 4:340-342): in the early stage of therapy, most patients will appear influenza-like syndrome, and clinical symptoms include fever, chills, headache, myalgia, gastrointestinal pain, etc. Nausea, vomiting and loss of appetite are common gastrointestinal reactions in the early stage of ordinary interferon α therapy. Fatigue occurs in more than 70% of patients during ordinary interferon α therapy. The main adverse reactions of the neuropsychiatric system are mental disorders, depression, trance, anxiety, irritability, etc. About 20% of patients receiving ordinary interferon α therapy may experience mild to moderate decreases in the total number of white blood cells, neutrophils, and platelets. Skin rash is the most common mucocutaneous lesion caused by ordinary interferon a, which is often manifested as a non-specific rash with pruritus; other manifestations include erythema at the injection site, skin ulceration, oral mucosal ulceration, cheilitis, and etc. Ordinary interferon α therapy can lead to thyroid dysfunction through autoimmune and non-autoimmune mechanisms, and hypothyroidism is the most common thyroid dysfunction. Ordinary interferon α can also induce autoimmune damage to islet β cells, thereby inducing diabetes. Other less common adverse reactions are interstitial pneumonia, retinopathy, hearing impairment and tinnitus, hair loss, diarrhea, and weight loss.

In order to improve the therapeutic effects of ordinary interferon α in the treatment of tumors and reduce the side effects, a beneficial exploration of the combination of ordinary interferon α with other tumor drugs has been carried out (Jun Guo, Advances in medical therapy of metastatic renal cancer, THE SECOND CHINESE CONGRESS OF MEDICAL ONCOLOGY, 2008:33-36). Among them, the regimen of using Bevacizumab combined with ordinary interferon α in the treatment of advanced renal cancer is the most successful. Two independent clinical trials have confirmed that using Bevacizumab combined with ordinary interferon α in the treatment of renal cancer can significantly prolong the PFS of patients compared with using ordinary interferons alone (10.2 vs 5.4 months, 8.5 vs 5.2 months). Based on the above results, in 2009, the US FDA approved Bevacizumab combined with ordinary interferons for the treatment of advanced renal cancer. However, the highest incidence of adverse reactions at grade 3 and above can reach 80% (Brian I. Rini, etc. Phase III Trial of Bevacizumab Plus Interferon Alfa Versus Interferon Alfa Monotherapy in Patients With Metastatic Renal Cell Carcinoma: Final Results of CALGB 90206, JOURNAL OF CLINICAL ONCOLOGY, 2010, VOL28, No. 13:2137-2143), so patients' compliance is poor, which limits the application of the regimen.

Human interferon α1b is a protein composed of 166 amino acids produced by human leukocytes, and its relative molecular weight is 19.382 kDa. Studies have shown that α1b type interferon is the main type of interferons produced by white blood cells of Chinese people after being attacked by a virus.

In the early 1980s, Yunde Hou et al. from the Institute of Virology of the Academy of Medical Science cloned the α1b interferon gene for the first time. This first genetically engineered protein drug in China, recombinant human interferon α1b, was jointly developed by the Institute of Virology and Shanghai Institute of Biological Products, and is one of the few new drugs with independent intellectual property rights in China.

Compared with ordinary interferon $\alpha_2$ products, ordinary interferon $\alpha_1$ has relatively low biological activity in vitro, but has a stronger in vivo effect with a wide range and less side effects. For example, the specific activities of ordinary interferon α2a and 2b in vitro are both $1\times10^8$ IU/mg, while the specific activity of ordinary interferon $\alpha_{1b}$ is only $1\times10^7$ IU/mg, which is 10% of the former two. In clinical application, the same weight of ordinary interferon ab has the same therapeutic effects of ordinary interferon α2a or 2b, and the side effects of ordinary interferon α1b are significantly less than the latter two (Kui-tang Tong, Interferon a treatment of melanoma, THE 17th NATIONAL ACADEMIC CONFERENCE ON INTERFERONS AND CYTOKINES, 2011:2-6). In the clinical trial of ordinary interferon $\alpha_{1b}$ in the treatment of hairy cell leukemia, the effective rate was 63.64%, the remission rate was 36.36%, and the adverse reaction was only a short-term low-grade fever, which subsided without medication, and other adverse reactions were not obvious. All adverse reactions were tolerated, and no patient discontinued its medication.

The results of phase I and II clinical trials in the United States showed that high-dose (500 μg/day) injection of ordinary interferon α1b had a certain therapeutic effect in the treatment of patients with metastatic renal cancer and multiple myeloma, and the adverse reactions were milder compared with other ordinary interferons (P. Masci, etc. Gene Modulatory Effects, Pharmacokinetics, and Clinical Tolerance of Interferon a-1b: A Second Member of the Interferon α Family. Clinical Pharmacology & Therapeutics. 2007. Vol. 81, No. 3:354-361).

Ordinary interferon α1b, like other ordinary interferons, also has the defects of being easily filtered by the glomerulus and having a short half-life in the human body due to its small molecular weight. In order to prolong the half-life and improve its therapeutic effects, ordinary interferon α1b was modified with the second-generation polyethylene glycol modifier to obtain an interferon α1b modified with a single PEG, which was named as PEGylated (PEG) interferon α1b. Studies have shown that its molecular weight is increased, and its half-life is significantly longer than that of unmodified ordinary interferon. The half-life of PEGylated (PEG) interferon α1b in rats is 13.98 hours, while that of ordinary interferon α1b is 1.84 hours; the half-life of PEGylated (PEG) interferon α1b in cynomolgus monkeys is 22.03±3.32 hours, while that of ordinary interferon α1b is 3.27±1.48 h. According to relevant research reports on PEG-modified recombinant therapeutic protein drugs on the market, the increase in molecular weight of such drugs is positively correlated with the improvement of their clinical efficacy.

In the present invention, preclinical pharmacodynamic studies in vitro and in vivo were conducted by using PEGylated (PEG) interferon α1b alone or using it in combination with other drugs.

The research results show that the combined use of PEGylated (PEG) interferon α1b with Bevacizumab (AVASTIN), Trastuzumab (HERCEPTIN) and other anti-tumor drugs not only has a synergistic effect in terms of efficacy, but also significantly reduces various side effects synergistically.

On the basis of the present invention, PEGylated (PEG) interferon α1b was observed in the tumor cell models in vitro to have a certain inhibitory effect on breast cancer cells, lung cancer cells, liver cancer cells and gastric cancer cells (inhibition rate 19.6%~58.4%).

In the in vivo breast cancer BT-474 tumor model of nude mice, the combination group of medium-dose PEGylated (PEG) interferon α1b (1 mg/kg) and Trastuzumab (HERCEPTIN) had a significant enhanced effect (170% inhibition rate in the combination group vs 98% inhibition rate in the medium-dose PEGylated (PEG) interferon α1b alone group vs 57% inhibition rate in the Trastuzumab (HERCEPTIN) alone group vs 156% inhibition rate in the high-dose PEGylated (PEG) interferon α1b alone group), and even 50% of the tumors in nude mice were observed to regress completely. These results not only confirmed that PEGylated (PEG) interferon α1b does had obvious anti-tumor effects, but also provided a solid foundation for its use in clinical tumor therapy. At the same time, the results also showed that the synergistic effect produced by combining PEGylated (PEG) interferon α1b with monoclonal antibodies can greatly reduce the dosage of PEGylated (PEG) interferon α1b (10 times lower), and thereby providing a wider range of dose selection for the combined use of PEGylated (PEG) interferon α1b with anti-tumor drugs such as monoclonal antibodies.

When PEGylated (PEG) interferon α1b and Bevacizumab (AVASTIN) were used in combination, it was observed that the therapeutic effects were significantly enhanced on the subcutaneous transplanted tumor model of human gastric cancer NCI-N87 in nude mice. At the same time, the results also showed that the synergistic effect produced by combining PEGylated (PEG) interferon α1b with monoclonal antibodies could greatly reduce the dosage of PEGylated (PEG) interferon α1b (10 times lower), and thereby providing a wider range of dose selection for the combined use of PEGylated (PEG) interferon α1b with anti-tumor drugs such as monoclonal antibodies.

In the liver cancer Huh-7 model of nude mice, the PEGylated (PEG) interferon α1b alone group has not shown any obvious inhibitory effects on tumors, and it suggests that although PEGylated (PEG) interferon α1b has anti-tumor activity, there are still some or great differences in the therapeutic effects of different tumors. However, when the PEG-interferon was used in combination with Bevacizumab (AVASTIN), it showed a certain synergistic effect.

Although PEGylated (PEG) interferon α2a and α2b have obvious advantages over ordinary interferons in the therapeutic effects of chronic hepatitis B and C, and have achieved great success. But in the field of cancer treatment, the effects are quite different.

In a phase III clinical study (T. K. Eigentler, etc. Adjuvant treatment with PEGylated interferon a-2a versus low-dose interferon a-2a in patients with high risk melanoma: a randomized phase III DeCOG trial, Annals of Oncology, 2016, 27:1625-1632), the efficacy and safety of administering PEGylated (PEG) interferon α2a or ordinary interferon 2a to high-risk melanoma patients were compared, and found that PEGylated (PEG) interferon α2a was not more effective than ordinary interferon α2a, while the side effects were more severe.

In another phase III clinical study (THOMAS M. H, etc. U.S. Food and Drug Administration Approval: Peginterferon-alfa-2b for the Adjuvant Treatment of Patients with Melanoma, The oncologist, 2012; 17:1323-1328), the mean recurrence-free survival of melanoma patients treated with PEGylated (PEG) interferon α2b in adjuvant therapy was 34.8 months, which was significantly longer than the 25.5 months of the observation group, but there was no significant improvement in overall survival. Although the incidence of serious adverse reactions in the treatment group was almost twice that of the observation group (33% vs 15%), in 2011 the US FDA still approved PEGylated (PEG) interferon α2b for adjuvant therapy of malignant melanoma patients with regional lymph nodes involvement. The PEGylated (PEG) interferon α2b was administered subcutaneously at 6 μg/kg every week, and maintained at 3 μg/kg every week after 8 consecutive injections of 6 μg/kg (NCCN Clinical Practice Guidelines in Oncology-Malignant Melanoma, 2nd Edition, 2018: MS-20). At present, there is only one approved regimen of PEGylated (PEG) interferon drugs for tumor indications, which shows that in the field of tumor treatment, the effects of different PEGylated (PEG) interferon subtypes and different tumor types on the therapeutic effects are significantly different, thus the results cannot be simply obtained by analogy.

Unexpectedly, unlike PEGylated (PEG) interferon α2a, the study of the present invention shows that the combined use of a PEGylated (PEG) interferon α1b with Bevacizumab (AVASTIN) or Trastuzumab (HERCEPTIN) can inhibit tumors synergistically, and significantly reduces the incidence or extent of their respective side effects (e.g. weight loss, fever, gastrointestinal adverse reactions, rash, etc.) at the same time.

All documents mentioned in the present invention are incorporated by reference herein as if each document were incorporated separately by reference. Furthermore, it should be understood that after reading the foregoing teachings of the invention, various changes or modifications may be made to the invention by those skilled in the art and that these equivalents also fall in the scope of the claims appended to this application.

The invention claimed is:

1. A method for treatment of a tumor, comprising a step of:

administering a combination of active ingredients to a subject in need thereof, wherein the active ingredients comprises a first active ingredient of polyethylene glycol (PEG)-interferon and a second active ingredient of a protooncogene product targeting inhibitor;

wherein the PEG-interferon is a PEG-interferon α1b;

the protooncogene product targeting inhibitor is selected from the group consisting of:

Bevacizumab, Trastuzumab, and combinations thereof;

when the protooncogene product targeting inhibitor is Bevacizumab, the tumor comprises gastric or liver cancer; when the protooncogene product targeting inhibitor is Trastuzumab, the tumor comprises breast cancer;

wherein the dose of the PEG-interferon is 50 ng/kg body weight to 10 mg/kg body weight, and the dose of the protooncogene product targeting inhibitor is 50 ng/kg body weight to 10 mg/kg body weight;

and wherein the PEG-interferon is administered to the subject before, during and/or after the administration of the protooncogene product targeting inhibitor.

2. The method of claim 1, wherein a mass ratio of the PEG-interferon to the protooncogene product targeting inhibitor is 1:100 to 500:1;

or, a ratio of the PEG-interferon to the protooncogene product targeting inhibitor is 1,000 IU/mg to 100 million IU/mg.

3. The method of claim 1, wherein the PEG-interferon and the protooncogene product targeting inhibitor are comprised in a pharmaceutical composition, and the pharmaceutical composition further comprises a pharmaceutically acceptable carrier.

4. The method of claim 1, wherein the protooncogene product targeting inhibitor is Bevacizumab, and the tumor comprises liver cancer.

5. The method of claim 1, wherein the protooncogene product targeting inhibitor is Trastuzumab, and the tumor comprises breast cancer.

6. The method of claim 1, wherein a ratio of the PEG-interferon to the protooncogene product targeting inhibitor is 10,000 IU/mg to 10 million IU/mg.

7. The method of claim 1, wherein a ratio of the PEG-interferon to the protooncogene product targeting inhibitor is 100,000 IU/mg to 5 million IU/mg or 200,000 IU/mg to 3 million IU/mg.

8. The method of claim 1, wherein the dose of the PEG-interferon is 0.1 mg/kg body weight, 1 mg/kg body weight, or 10 mg/kg body weight.

9. The method of claim 1, wherein the dose of Bevacizumab is 10 mg/kg body weight.

10. The method of claim 1, wherein the dose of Trastuzumab is 5 mg/kg body weight.

11. The method of claim 1, wherein the dose of the PEG-interferon is 1 mg/kg body weight, and the dose of Bevacizumab is 10 mg/kg body weight.

12. The method of claim 1, wherein the dose of the PEG-interferon is 1 mg/kg body weight, and the dose of Trastuzumab is 5 mg/kg body weight.

* * * * *